(12) United States Patent
Reynolds et al.

(10) Patent No.: US 8,106,152 B2
(45) Date of Patent: Jan. 31, 2012

(54) ANTIMICROBIAL COMPOSITION

(75) Inventors: Eric Charles Reynolds, Balwyn (AU); Stuart Geoffrey Dashper, Brunswick East (AU); Rita Ann Paolini, Kew (AU)

(73) Assignee: Dairy Australia Limited, Southbank, Victoria (AU)

( * ) Notice: Subject to any disclaimer, the term of this patent is extended or adjusted under 35 U.S.C. 154(b) by 886 days.

(21) Appl. No.: 10/596,623

(22) PCT Filed: Dec. 15, 2004

(86) PCT No.: PCT/AU2004/001764
§ 371 (c)(1), (2), (4) Date: Jun. 6, 2008

(87) PCT Pub. No.: WO2005/058344
PCT Pub. Date: Jun. 30, 2005

(65) Prior Publication Data
US 2009/0246150 A1    Oct. 1, 2009

(30) Foreign Application Priority Data
Dec. 19, 2003    (AU) ............................. 2003907002

(51) Int. Cl.
*A61K 38/00* (2006.01)

(52) U.S. Cl. ........ 530/300; 530/350; 530/832; 530/360; 435/32

(58) Field of Classification Search ........................ None
See application file for complete search history.

(56) References Cited

U.S. PATENT DOCUMENTS

| | | | |
|---|---|---|---|
| 4,992,420 A | 2/1991 | Neeser | |
| 4,994,441 A | 2/1991 | Neeser | |
| 5,583,198 A | 12/1996 | Whittaker | |
| 5,824,292 A | 10/1998 | Carr et al. | |
| 5,846,732 A | 12/1998 | Collin et al. | |
| 6,096,870 A | 8/2000 | Mozaffar et al. | |
| 2003/0195150 A1 | 10/2003 | Reynolds et al. | |

FOREIGN PATENT DOCUMENTS

| | | |
|---|---|---|
| EP | 0 737 470 A1 | 10/1996 |
| JP | 07278013 A | 10/1995 |
| JP | H7-257938 | 10/1995 |
| JP | H10-114812 | 5/1998 |
| JP | 2000-254988 | 9/2000 |
| JP | 2001-233720 | 8/2001 |
| WO | WO 9109837 | 7/1991 |
| WO | WO 95/31556 A1 | 11/1995 |
| WO | 09840406 | 9/1998 |
| WO | 99/26971 * | 6/1999 |
| WO | WO 00/06108 A1 | 2/2000 |
| WO | WO 00/18365 | 4/2000 |
| WO | WO 00/72685 | 12/2000 |
| WO | WO02094204 | 11/2002 |

OTHER PUBLICATIONS

Cummins et al (J.Clin. Periodontol. 1991. 18: 455-461).*
Phan et al (Oral Microbiol. 2004. Immunol. 19: 31-38).*
Chothia et al (The EMBO Journal, 1986, 5/4:823-26).*
Boman, et al. Antibacterial Peptides:Key components needed in immunity. Cell, (1991), vol. 65, pp. 205-207.
Jelen. Nordic Milk Protein Conference. Trend in Food Science & Technology, (1996), vol. 7, pp. 171-173.
Lahov and Regelson. Antibacterial and Immunostimulating Casein-derived Substances from Milk: Casecidin, Isracidin Peptites. Fd Chem. Toxic, (1996), vol. 34, No. 1, pp. 131-145.
Yvon, et al. Effects of Caseinomacropeptide (CMP) on Digestion Regulation. Reprod Nutr Dev (1994), vol. 34, pp. 527-537.
Adamson et al. The analysis of multiple phonsphoseryl-containing casein peptides using capillary zone electrophoresis. Journal of Chromatography, 1993, vol. 646, pp. 391-396.
Addeo et al. Structure primaire du caséinomacropepetide de la caséine x de buffle. Biochimie, 1977, vol. 59, pp. 375-379.
Alexander, et al. Isolatiion and characterization of the bovine kappa-casein gene. Eur. J. Biochem., 1998, vol. 178, pp. 395-401.
Bergstom et al. Cloning and sequencing of human k-casein cDNA. DNA Sequence—J. DNA Sequencing and Mapping, 1992, vol. 3 pp. 245-246.
Bowie et al. Deciphering the message in protein sequences: tolerance to amino acid substitutions. Science, 1990, vol. 247, pp. 1306-1310.
Ferjancic-Biagini et al. Acylation of food proteins and hydrolysis by digestive enzymes: A review. Journal of Food Biochemistry, 1998, vol. 22, pp. 331-345.
Jimenez-Flores et al. Cloning and sequence analysis of bovine β-casein cDNA. Biochemical and Biophysical Research Communications, 1987, vol. 142, No. 2, pp. 616-621.
Grosclaude et al. Caractérisation des variants génétiques des caséines as1 et βbovines. Eur. J. Biochem., 1972, vol. 26, pp. 328-337.
Migliore-Samour et al. Biologically active casein peptides implicated in immunomodulation. Journal of Diary Research, 1989, vol. 56, pp. 357-362.
Molle et al. Heterogeneity of the bovine k-casein caseinomacropeptide, resolved by liquid chomatography on-line with electrospray ionization mass spectromwtry. Journal of Chromatography A, 1995, pp. 223-230.
Minkiewicz et al. Reserved-phase high-performance liquid chromatographic separation of bovine _k-casein macropeptide and characterization of isolated fractions. Journal of Chromatography A, 1996, vol. 743, pp. 123-135.
Nagaune et al. Preparation of anti-bovine β-casein monoclonal antibody and analysis of the interaction between the antibody and β-casein fragment. Agric. Biol. Chem, 1998, vol. 5, No. 10, pp. 2577-2581.
Ota et al. Turbidity of stem bromelain toward casein solution. Department of Biochemistry, 1986, pp. 29-40.
Otani et al. The common antigenic site of bovine and human β-caseins. Michwissenschaft, 1998, vol. 43, No. 11, pp. 705-707.
Wells et al. Additivity of mutational effects in proteins. Biochemistry, 1990, vol. 29, No. 37, pp. 8509-8517.
Database Uniport Kappa-Casein (fragment) May 1, 1997, Wollard J.R. et al., retrieved from EBI Database accession No. P79094, CP002293161.

(Continued)

*Primary Examiner* — Jennifer Graser
(74) *Attorney, Agent, or Firm* — Paula A. Borden; Bozicevic Field & Francis LLP

(57) ABSTRACT

The present invention relates to novel antimicrobial composition comprising a peptide which can be obtained from the milk protein casein or chemically synthesised or produced by recombinant DNA technology and a divalent cation.

17 Claims, 7 Drawing Sheets

OTHER PUBLICATIONS

Figure 1:
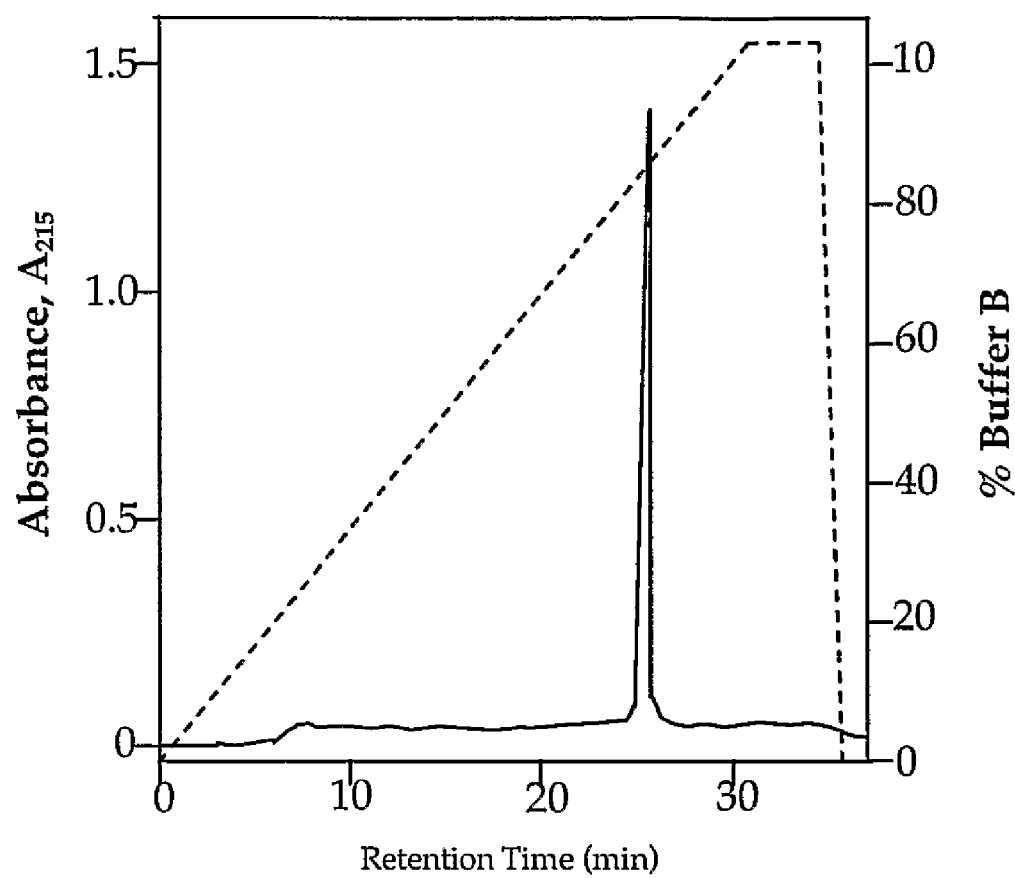

Database Uniport Kappa-Casein (fragment) May 1, 1997, Wollard J.R. et al., retrieved from EBI Database accession No. P79094, CP002293162.

Willis et al. Manipulation and Expression of Genes in Eukaryotes (1983), p. 25-26.

Addy et al. Effects of a Zinc Citrate Mouthwash on Dental Plaque and Salivary Bacteria. Journal of Clinical Periodontology, 1980, vol. 7, pp. 309-315.

Addy, Rationale for chemotherapy in the treatment of periodontal disease, In: Periodontology Today (Guggenheim B (ed)), 1988, pp. 281-289, Karger, Basel.

Bevins et al. Peptides from frog skin. Annual Review of Biochemistry, 1990, vol. 59, pp. 395-414.

Boman et al. Cell-free immunity in insects. 1987, Annual Review of Microbiology, vol. 41, pp. 103-126.

Brown et al. Periodontal diseases in the US in 1981: Prevalence, severity, extent and role in tooth mortality. Journal of Periodontology, 1989, vol. 60, pp. 363-370.

Casteels et al. Apidaecins: antibacterial peptides from honeybees. The EMBO Journal, 1989, vol. 8, pp. 2387-2391.

Christersson et al. Specific subgingival bacteria and diagnosis of gingivitis and periodontitis. Journal of Dental Research, 1989, vol. 68, pp. 1633-1639.

Clark et al. Ranalexin. A novel antimicrobial peptide from bullfrog (Rana catesbeiana) skin, structurally related to the bacterial antibiotic, polymyxin. The Journal of Biological Chemistry, 1994, vol. 269, pp. 10849-10855.

Corbet et al. The Role of Supragingival Plaque in the Control of Progressive Periodontal-Disease—a Review, Journal of Clinical Periodontology 1993, vol. 20, pp. 307-313.

Creamer et al. Relationship between milk protein polymorphism and physico-chemical properties. Milk Protein Polymorphism: International Dairy Federation Special Issue, 1997, vol. 9702, pp. 110-123.

Cummins et al. Delivery of Antiplaque Agents from Dentifrices, Gels, and Mouthwashes. Journal of Dental Research, 1992, vol. 71, pp. 1439-1449.

Eldridge et al. Efficacy of an alcohol-free chlorhexidine mouthrinse as an antimicrobial agent. Journal of Prosthetic Dentistry, 1998, vol. 80, pp. 685-690.

Folch et al. A Simple Method for the Isolation and Purification of Total Lipides from Animal Tissues. The Journal of Biological Chemistry, 1957, vol. 226, pp. 497-509.

Giertesen et al. Inhibition of plaque formation and plaque acidogenicity by zinc and chlorhexidine combinations. Scandinavian Journal of Dental Research, 1998, vol. 96, pp. 541-550.

Goumon et al. The C-terminal bisphosphorylated proenkephalin-A-(209-237)-peptide from adrenal medullary chromaffin granules possesses antibacterial activity. European Journal of Biochemistry, 1996, vol. 235, pp. 516-525.

Hogg. Chemical control of plaque. Dental Update, 1990, vol. 17, pp. 332-334.

Hope et al. Measuring the thickness of an outer layer of viable bacteria in an oral biofilm by viability mapping. Journal of Microbiological Methods, 2003, vol. 54, pp. 403-410.

Loe. The Gingival Index, the plaque index and the retention index systems. Journal of Periodontology, 1976, vol. 38, pp. 610-616.

Malkoski et al. Kappacin, a novel antibacterial peptide from bovine milk. Antimicrobial Agents and Chemotherapy, 2001, vol. 45, pp. 2309-2315.

Marsh. Dentifrices containing new agents for the control of plaque and gingivitis: microbiological aspects. Journal of Clinical Periodontology 1991, vol. 18, pp. 462-467.

Migliore-Samour et al. Biologically active casein peptides implicated in immunomodulation. Journal of Dairy Research, 1989, vol. 56, pp. 357-362.

Moore et al. Bacteriology of human gingivitis. Journal of Dental Research, 1987, vol. 66, pp. 989-995.

Mor et al. Isolation and structure of novel defensive peptides from frog skin. European Journal of Biochemistry, 1994, vol. 219, pp. 145-154.

Nikaido et al. Identification and Characterization of Porins in Pseudomonas-Aeruginosa. Journal of Biological Chemistry, 1991, vol. 266, pp. 770-779.

Plowman et al. Solution conformation of a peptide corresponding to bovine kappa-casein B residues 130-153 by circular dichroism spectroscopy and H-1-nuclear magnetic resonance spectroscopy. Journal of Dairy Research, 1997, vol. 64, pp. 377-397.

Rogers et al. The utilisation of casein and amino acids by *Streptococcus sanguis* P4A7in continuous culture. Journal of General Microbiology. 1990, vol. 136, pp. 2545-2550.

Romeo D et al. Structure and bactericidal activity of an antibiotic dodecapeptide purified from bovine neutophils. The Journal of Biological Chemistry, 1988, vol. 263, pp. 9573-9575.

Shu et al. Role of urease enzymes in stability of a 10-species oral biofilm consortium cultivated in a constant-depth film fermenter. Infection and Immunity, 2003, vol. 71, pp. 7188-7192.

Simmaco et al. A family of bombinin-related peptides from the skin of *Bombina variegata*. European Journal of Biochemistry, 1991, vol. 199, pp. 217-222.

Smallcombe et al. WET solvent suppression and its applications to LC NMR and high-resolution NMR spectroscopy. Journal of Magnetic Resonance Series A, 1995, vol. 117, pp. 295-303.

Smith et al. Structural features of bovine caseinomacropeptide A and B by H-1 nuclear magnetic resonance spectroscopy. Journal of Dairy Research, 2002, vol. 69, pp. 85-94.

Spencer et al. A socio-dental study of adult periodontal health: Melbourne 1985. Community Dental Health Monograph No. 5, 1985, Melbourne University Press.

Strub et al. Antibacterial activity of glycosylated and phosphorylated chromogranin A-derived peptide 173-194 from bovine adrenal medullary chromaffin granules. Journal of Biological Chemistry, 1996, vol. 271, pp. 28533-28540.

Svedberg, et al. Demonstration of B-casomorphin immunoreactive materials in in vivo digests of bovine milk and in small intestine contents after bovine milk ingestion in adult humans. Peptides, 1985, vol. 6, pp. 825-830.

Talbo et al. MALDI-PSD-MS analysis of the phosphorylation sites of caseinomacropeptide. Peptides, 2001, vol. 22, pp. 1093-1098.

Wilson. Susceptibility of oral bacterial biofilms to antimicrobial agents. Journal of Medical Microbiology, 1996, vol. 44, pp. 79-87.

Wimpenny et al. Modeling spatial gradients. Structure and function of biofilms (W. Characklis and P. Wlderer (ed.)), 1989, pp. 111-127, John Wiley and Sons, Chichester.

Zanetti et al. Molecular cloning and chemical synthesis of a novel antibacterial peptide derived from pig myeloid cells. The Journal of Biological Chemistry, 1994, vol. 269, pp. 7855-7858.

Zucht et al. Casocidin-I: a casein-alpha s2 derived peptide exhibits antibacterial activity. FEBS Letters. 1995, vol. 25,372 (2-3), pp. 185-188.

Dashper Stuart G et al: "Divalent metal cations increase the activity of the antimicrobial peptide kappacin", Antimicrobial Agents and Chemotherapy, vol. 49, No. 6, Jun. 2005, pp. 2322-2328.

* cited by examiner

ANTIMICROBIAL COMPOSITION

FIELD OF THE INVENTION

The present invention relates to novel antimicrobial composition comprising a peptide which can be obtained from the milk protein casein or chemically synthesised or produced by recombinant DNA technology and a divalent cation. These compositions can be used in foods as antimicrobial preservatives, in oral care products (eg. toothpaste, mouthwash, dental floss) for the control of dental plaque and suppression of pathogens associated with dental caries and periodontal diseases.

BACKGROUND OF THE INVENTION

Kappacin, the nonglycosylated, phosphorylated forms of bovine caseinomacropeptide (CMP), has been shown to have antibacterial activity in vitro against both Gram-negative and Gram-positive oral bacteria (Malkoski et al., 2001). CMP is a 64 amino acid polypeptide released from bovine κ-casein by chymosin hydrolysis of the peptide bond between Phe$^{105}$ and Met$^{106}$. It comprises the 106-169 C-terminal fragment of κ-casein and contains all the post-translational modification sites found in κ-casein. CMP is both variably phosphorylated and glycosylated (Pisano et al., 1984; Saito and Itoh, 1992; Talbo et al., 2001). CMP is completely phosphorylated at Ser$^{149}$ and partially phosphorylated (10%) at Ser$^{127}$ as determined by MALDI-PSD mass spectrometry (Talbo et al., 2001). Additionally there are at least six genetic variants of κ-casein, with variants A and B being by far the most common (Creamer and Harris, 1997). Variants A and B differ at residues 136 and 148 where the hydrophilic residues Thr$^{136}$ and Asp$^{148}$ of variant A are substituted by the hydrophobic residues Ile$^{136}$ and Ala$^{148}$ in variant B. The antibacterial active region of Kappacin was demonstrated to be residues 138-158 as determined using the synthetic peptide Ser(P)$^{149}$κ-casein-A(138-158). Phosphorylation of Ser$^{149}$ was shown to be essential for antibacterial activity using the synthetic peptide κ-casein-A(138-158) (Malkoski et al., 2001). The MIC of CMP variant A against *Streptococcus mutans* 0.68 mg/ml (100 μM) whilst variant B was less active with a MIC of 1.04 mg/ml (154 μM) (Malkoski et al., 2001).

The mechanism by which Kappacin inhibits bacterial growth is still unclear. Kappacin was found to be most effective against *S. mutans* at slightly acidic growth pH. The non-glycosylated, κ-casein-B(130-158) has been proposed to form an amphipathic α-helix, especially in the presence of trifluoroethanol (TFE; Plowman, 1997). This characteristic could help to explain its antibacterial activity if it works as a surface-active agent, creating pores in the cell membrane. This mode of action has been proposed for the majority of the cationic antimicrobial peptides isolated to date. However Kappacin is an anionic peptide that does not exhibit sequence similarity with the better known cationic an tibacterial peptides and apart from a possible propensity to form an amphipathic helical structure does not posses any of the other characteristics of these peptides. Kappacin does share some characteristics with the recently discovered anionic antibacterial peptides, especially enkelytin. This peptide, like Kappacin, contains a number of glutamyl residues and phosphorylation is essential for antibacterial activity (Goumon, 1996; Goumon, 1998; Strub, 1996). The structure of the phosphorylated form of enkelytin has not been determined, although phosphorylation has been proposed to change the conformation of the peptide through electrostatic repulsion or by divalent metal ion binding (Goumon, 1998; Kieffer, 1998). It remains unclear how the negatively charged antibacterial peptides, including Kappacin, interact with the bacterial cell surface.

SUMMARY OF THE INVENTION

The present inventors investigated the effect of pH and divalent metal cations on the antibacterial activity and structure of the peptide. The present inventors were able to show a synergistic effect between the peptides and divalent cations.

Accordingly, in a first aspect the present invention consists in an antimicrobial composition, the composition comprising a divalent cation and a peptide, the peptide being non-glycosylated, less than about 100 amino acids, preferably less than about 70 amino acids, and comprising an amino acid sequence selected from the group consisting of:—

```
                                            (SEQ ID NO: 1)
Ala Val Glu Ser Thr Val Ala Thr Leu Glu Ala Ser(P)
Pro Glu Val Ile Glu Ser Pro Pro Glu, (SEQ ID NO: 2)
Ala Val Glu Ser Thr Val Ala Thr Leu Glu Asp Ser(P)
Pro Glu Val Ile Glu Ser Pro Pro Glu,
``` and conservative substitutions therein.

In a preferred embodiment of the present invention the peptide comprises an amino acid sequence selected from the group consisting of:—

```
                                            (SEQ ID NO: 1)
Ala Val Glu Ser Thr Val Ala Thr Leu Glu Ala Ser(P)
Pro Glu Val Ile Glu Ser Pro Pro Glu,
and
                                            (SEQ ID NO: 2)
Ala Val Glu Ser Thr Val Ala Thr Leu Glu Asp Ser(P)
Pro Glu Val Ile Glu Ser Pro Pro Glu.
```

In a further preferred embodiment of the present invention the peptide comprises an amino acid sequence selected from the group consisting of:—

```
                                                            (SEQ ID NO: 3)
Met Ala Ile Pro Pro Lys Lys Asn Gln Asp Lys Thr Glu Ile Pro Thr Ile Asn Thr Ile Ala Ser Gly
Glu Pro Thr Ser Thr Pro Thr Ile Glu Ala Val Glu Ser Thr Val Ala Thr Leu Glu Ala Ser(P) Pro
Glu Val Ile Glu Ser Pro Pro Glu Ile Asn Thr Val Gln Val Thr Ser Thr Ala Val;

(SEQ ID NO: 4)
Met Ala Ile Pro Pro Lys Lys Asn Gln Asp Lys Thr Glu Ile Pro Thr Ile Asn Thr Ile Ala Ser(P)
Gly Glu Pro Thr Ser Thr Pro Thr Ile Glu Ala Val Glu Ser Thr Val Ala Thr Leu Glu Ala Ser(P)
Pro Glu Val Ile Glu Ser Pro Pro Glu Ile Asn Thr Val Gln Val Thr Ser Thr Ala Val;
```

```
                                                                  (SEQ ID NO: 5)
Met Ala Ile Pro Pro Lys Lys Asn Gln Asp Lys Thr Glu Ile Pro Thr Ile Asn Thr Ile Ala Ser Gly
Glu Pro Thr Ser Thr Pro Thr Thr Glu Ala Val Glu Ser Thr Val Ala Thr Leu Glu Asp Ser(P) Pro
Glu Val Ile Glu Ser Pro Pro Glu Ile Asn Thr Val Gln Val Thr Ser Thr Ala Val;

(SEQ ID NO: 6)
Met Ala Ile Pro Pro Lys Lys Asn Gln Asp Lys Thr Glu Ile Pro Thr Ile Asn Thr Ile Ala Ser(P)
Gly Glu Pro Thr Ser Thr Pro Thr Thr Glu Ala Val Glu Ser Thr Val Ala Thr Leu Glu Asp Ser(P)
Pro Glu Val Ile Glu Ser Pro Pro Glu Ile Asn Thr Val Gln Val Thr Ser Thr Ala Val;

(SEQ ID NO: 7)
Thr Glu Ile Pro Thr Ile Asn Thr Ile Ala Ser Gly Glu Pro Thr Ser Thr Pro Thr Ile Glu Ala Val
Glu Ser Thr Val Ala Thr Leu Glu Ala Ser(P) Pro Glu Val Ile Glu Ser Pro Pro Glu Ile Asn Thr
Val Gln Val Thr Ser Thr Ala Val;

(SEQ ID NO: 8)
Thr Glu Ile Pro Thr Ile Asn Thr Ile Ala Ser(P) Gly Glu Pro Thr Ser Thr Pro Thr Ile Glu Ala
Val Glu Ser Thr Val Ala Thr Leu Glu Ala Ser(P) Pro Glu Val Ile Glu Ser Pro Pro Glu Ile Asn
Thr Val Gln Val Thr Ser Thr Ala Val;

(SEQ ID NO: 9)
Thr Glu Ile Pro Thr Ile Asn Thr Ile Ala Ser Gly Glu Pro Thr Ser Thr Pro Thr Thr Glu Ala Val
Glu Ser Thr Val Ala Thr Leu Glu Asp Ser(P) Pro Glu Val Ile Glu Ser Pro Pro Glu Ile Asn Thr
Val Gln Val Thr Ser Thr Ala Val;

(SEQ ID NO: 10)
Thr Glu Ile Pro Thr Ile Asn Thr Ile Ala Ser(P) Gly Glu Pro Thr Ser Thr Pro Thr Thr Glu Ala
Val Glu Ser Thr Val Ala Thr Leu Glu Asp Ser(P) Pro Glu Val Ile Glu Ser Pro Pro Glu Ile Asn
Thr Val Gln Val Thr Ser Thr Ala Val;
``` and conservative substitutions therein.

It is further preferred that the peptide comprises an amino acid sequence selected from the group consisting of:—

```
                                                                  (SEQ ID NO: 3)
Met Ala Ile Pro Pro Lys Lys Asn Gln Asp Lys Thr Glu Ile Pro Thr Ile Asn Thr Ile Ala Ser Gly
Glu Pro Thr Ser Thr Pro Thr Ile Glu Ala Val Glu Ser Thr Val Ala Thr Leu Glu Ala Ser(P) Pro
Glu Val Ile Glu Ser Pro Pro Glu Ile Asn Thr Val Gln Val Thr Ser Thr Ala Val;

(SEQ ID NO: 4)
Met Ala Ile Pro Pro Lys Lys Asn Gln Asp Lys Thr Glu Ile Pro Thr Ile Asn Thr Ile Ala Ser(P)
Gly Glu Pro Thr Ser Thr Pro Thr Ile Glu Ala Val Glu Ser Thr Val Ala Thr Leu Glu Ala Ser(P)
Pro Glu Val Ile Glu Ser Pro Pro Glu Ile Asn Thr Val Gln Val Thr Ser Thr Ala Val;

(SEQ ID NO: 5)
Met Ala Ile Pro Pro Lys Lys Asn Gln Asp Lys Thr Glu Ile Pro Thr Ile Asn Thr Ile Ala Ser Gly
Glu Pro Thr Ser Thr Pro Thr Thr Glu Ala Val Glu Ser Thr Val Ala Thr Leu Glu Asp Ser(P) Pro
Glu Val Ile Glu Ser Pro Pro Glu Ile Asn Thr Val Gln Val Thr Ser Thr Ala Val;

(SEQ ID NO: 6)
Met Ala Ile Pro Pro Lys Lys Asn Gln Asp Lys Thr Glu Ile Pro Thr Ile Asn Thr Ile Ala Ser(P)
Gly Glu Pro Thr Ser Thr Pro Thr Thr Glu Ala Val Glu Ser Thr Val Ala Thr Leu Glu Asp Ser(P)
Pro Glu Val Ile Glu Ser Pro Pro Glu Ile Asn Thr Val Gln Val Thr Ser Thr Ala Val;

(SEQ ID NO: 7)
Thr Glu Ile Pro Thr Ile Asn Thr Ile Ala Ser Gly Glu Pro Thr Ser Thr Pro Thr Ile Glu Ala Val
Glu Ser Thr Val Ala Thr Leu Glu Ala Ser(P) Pro Glu Val Ile Glu Ser Pro Pro Glu Ile Asn Thr
Val Gln Val Thr Ser Thr Ala Val;

(SEQ ID NO: 8)
Thr Glu Ile Pro Thr Ile Asn Thr Ile Ala Ser(P) Gly Glu Pro Thr Ser Thr Pro Thr Ile Glu Ala
Val Glu Ser Thr Val Ala Thr Leu Glu Ala Ser(P) Pro Glu Val Ile Glu Ser Pro Pro Glu Ile Asn
Thr Val Gln Val Thr Ser Thr Ala Val;

(SEQ ID NO: 9)
Thr Glu Ile Pro Thr Ile Asn Thr Ile Ala Ser Gly Glu Pro Thr Ser Thr Pro Thr Thr Glu Ala Val
Glu Ser Thr Val Ala Thr Leu Glu Asp Ser(P) Pro Glu Val Ile Glu Ser Pro Pro Glu Ile Asn Thr
Val Gln Val Thr Ser Thr Ala Val;
and (SEQ ID NO: 10)
Thr Glu Ile Pro Thr Ile Asn Thr Ile Ala Ser(P) Gly Glu Pro Thr Ser Thr Pro Thr Thr Glu Ala
Val Glu Ser Thr Val Ala Thr Leu Glu Asp Ser(P) Pro Glu Val Ile Glu Ser Pro Pro Glu Ile Asn
Thr Val Gln Val Thr Ser Thr Ala Val.
```

In yet a further preferred embodiment of the present invention the peptide is selected from the group consisting of:—

(SEQ ID NO: 3)
Met Ala Ile Pro Pro Lys Lys Asn Gln Asp Lys Thr Glu Ile Pro Thr Ile Asn Thr Ile Ala Ser Gly
Glu Pro Thr Ser Thr Pro Thr Ile Glu Ala Val Glu Ser Thr Val Ala Thr Leu Glu Ala Ser(P) Pro
Glu Val Ile Glu Ser Pro Pro Glu Ile Asn Thr Val Gln Val Thr Ser Thr Ala Val;

(SEQ ID NO: 4)
Met Ala Ile Pro Pro Lys Lys Asn Gln Asp Lys Thr Glu Ile Pro Thr Ile Asn Thr Ile Ala Ser(P)
Gly Glu Pro Thr Ser Thr Pro Thr Ile Glu Ala Val Glu Ser Thr Val Ala Thr Leu Glu Ala Ser(P)
Pro Glu Val Ile Glu Ser Pro Pro Glu Ile Asn Thr Val Gln Val Thr Ser Thr Ala Val;

(SEQ ID NO: 5)
Met Ala Ile Pro Pro Lys Lys Asn Gln Asp Lys Thr Glu Ile Pro Thr Ile Asn Thr Ile Ala Ser Gly
Glu Pro Thr Ser Thr Pro Thr Thr Glu Ala Val Glu Ser Thr Val Ala Thr Leu Glu Asp Ser(P) Pro
Glu Val Ile Glu Ser Pro Pro Glu Ile Asn Thr Val Gln Val Thr Ser Thr Ala Val;

(SEQ ID NO: 6)
Met Ala Ile Pro Pro Lys Lys Asn Gln Asp Lys Thr Glu Ile Pro Thr Ile Asn Thr Ile Ala Ser(P)
Gly Glu Pro Thr Ser Thr Pro Thr Thr Glu Ala Val Glu Ser Thr Val Ala Thr Leu Glu Asp Ser(P)
Pro Glu Val Ile Glu Ser Pro Pro Glu Ile Asn Thr Val Gln Val Thr Ser Thr Ala Val;

(SEQ ID NO: 7)
Thr Glu Ile Pro Thr Ile Asn Thr Ile Ala Ser Gly Glu Pro Thr Ser Thr Pro Thr Ile Glu Ala Val
Glu Ser Thr Val Ala Thr Leu Glu Ala Ser(P) Pro Glu Val Ile Glu Ser Pro Pro Glu Ile Asn Thr
Val Gln Val Thr Ser Thr Ala Val;

(SEQ ID NO:8);
Thr Glu Ile Pro Thr Ile Asn Thr Ile Ala Ser(P) Gly Glu Pro Thr Ser Thr Pro Thr Ile Glu Ala
Val Glu Ser Thr Val Ala Thr Leu Glu Ala Ser(P) Pro Glu Val Ile Glu Ser Pro Pro Glu Ile Asn
Thr Val Gln Val Thr Ser Thr Ala Val;

(SEQ ID NO: 9)
Thr Glu Ile Pro Thr Ile Asn Thr Ile Ala Ser Gly Glu Pro Thr Ser Thr Pro Thr Thr Glu Ala Val
Glu Ser Thr Val Ala Thr Leu Glu Asp Ser(P) Pro Glu Val Ile Glu Ser Pro Pro Glu Ile Asn Thr
Val Gln Val Thr Ser Thr Ala Val;

(SEQ ID NO: 10)
Thr Glu Ile Pro Thr Ile Asn Thr Ile Ala Ser(P) Gly Glu Pro Thr Ser Thr Pro Thr Thr Glu Ala
Val Glu Ser Thr Val Ala Thr Leu Glu Asp Ser(P) Pro Glu Val Ile Glu Ser Pro Pro Glu Ile Asn
Thr Val Gln Val Thr Ser Thr Ala Val;

(SEQ ID NO: 1)
Ala Val Glu Ser Thr Val Ala Thr Leu Glu Ala Ser(P) Pro Glu Val Ile Glu Ser Pro Pro;
and (SEQ ID NO: 2)
Ala Val Glu Ser Thr Val Ala Thr Leu Glu Asp Ser(P) Pro Glu Val Ile Glu Ser Pro Pro.

The divalent cation is preferably selected from the group consisting of $Zn^{2+}$, $Ca^{2+}$, $Cu^{2+}$, $Ni^{2+}$, $Co^{2+}$, $Fe^{2+}$, $Sn^{2+}$, and $Mn^{2+}$. In addition, the divalent cation may be in association with fluoride such as $SnF^+$ and $CuF^+$. It is currently preferred, however, that the divalent cation is $Ca^{2+}$ or $Zn^{2+}$.

It is further preferred that the molar ratio of the divalent cation to the peptide is in the range of 0.5:1.0 to 15.0:1.0, preferably in the range of 0.5:1.0 to 4.0:1.0. It is further preferred that the molar ratio of the divalent cation to the peptide is in the range of 1.0:1.0 to 4.0:1.0, preferably 1.0:1.0 to 2.0:1.0.

In a still further preferred embodiment the composition further comprises a pharmaceutically-acceptable carrier. Such compositions may be dental, intra-oral compositions, therapeutic anti-infective compositions for topical and systemic application. Dental compositions or therapeutic compositions may be in the form of a gel, liquid, solid, powder, cream or lozenge. Therapeutic compositions may also be in the form of tablets or capsules.

In a further aspect, there is provided a method of treating or preventing dental caries or periodontal disease in a subject, the method comprising the step of administering the composition of the present invention to the teeth or gums of a subject in need of such treatments. Topical administration of the composition is preferred.

As it is the physical nature of the peptides rather than the specific sequence of the peptide which results in their antimicrobial activity so called conservative substitutions may be made in the peptide sequence with no substantial loss of activity. It is intended that such conservative substitutions which do not result in a substantial loss of activity are encompassed in the present invention.

Whilst the concept of conservative substitution is well understood by the person skilled in the art, for the sake of clarity conservative substitutions are those set out below.

Gly, Ala, Val, Ile, Leu, Met;

Asp, Glu, Ser;

Asn, Gln;

Ser, Thr;

Lys, Arg, His;

Phe, Tyr, Trp, His;
and

Pro, Nα-alkalamino acids.

The compositions of the present invention have a number of applications, for example, they can be used in foods as antimicrobial preservatives, in oral care products (toothpastes and mouthrinses) for the control of dental plaque and suppression of pathogens associated with dental caries and periodontal diseases. The antimicrobial compositions of the present invention may also be used in pharmaceutical preparations (eg, topical and systemic anti-infective medicines).

Throughout this specification the word "comprise", or variations such as "comprises" or "comprising", will be understood to imply the inclusion of a stated element or integer or group of elements or integers but not the exclusion of any other element or integer or group of elements or integers.

DETAILED DESCRIPTION OF THE INVENTION

The present invention relates to an antimicrobial composition comprising a divalent cation and at least one peptide. These peptides were initially derived from casein, κ-casein (106-169) [Table 1].

The peptides Ser(P)$^{149}$ κ-casein (117-169) and Ser(P)$^{127}$, Ser(P)$^{149}$ κ-casein (117-169) can be purified from a tryptic digest of bovine casein using standard chromatographic procedures of anion exchange and reversed-phase chromatography (HPLC). Ser(P)$^{149}$ κ-casein (106-169) and Ser(P)$^{127}$, Ser(P)$^{149}$ κ-casein (106-169) can also be prepared from cheese whey and rennet whey by removal of the whey proteins by ultrafiltration, or acid precipitation followed by reversed-phase HPLC purification of the phosphopeptides. The peptides can be prepared from casein of other species, eg. goat, sheep etc.

TABLE 1

Casein Antimicrobial Peptides

| Peptide | Sequence$^a$ |
|---|---|
| Ser(P)$^{149}$ κ-casein B (106-169) | Met Ala Ile Pro Pro Lys Lys Asn Gln Asp Lys Thr Glu Ile Pro Thr Ile Asn Thr Ile Ala Ser Gly Glu Pro Thr Ser Thr Pro Thr Ile Glu Ala Val Glu Ser Thr Val Ala Thr Leu Glu Ala Ser(P) Pro Glu Val Ile Glu Ser Pro Pro Glu Ile Asn Thr Val Gln Val Thr Ser Thr Ala Val (SEQ ID NO: 3) |
| Ser(P)$^{127}$, Ser(P)$^{149}$ κ-casein B (106-169) | Met Ala Ile Pro Pro Lys Lys Asn Gln Asp Lys Thr Glu Ile Pro Thr Ile Asn Thr Ile Ala Ser(P) Gly Glu Pro Thr Ser Thr Pro Thr Ile Glu Ala Val Glu Ser Thr Val Ala Thr Leu Glu Ala Ser(P) Pro Glu Val Ile Glu Ser Pro Pro Glu Ile Asn Thr Val Gln Val Thr Ser Thr Ala Val (SEQ ID NO: 4) |
| Ser(P)$^{149}$, κ-casein A (106-169) | Met Ala Ile Pro Pro Lys Lys Asn Gln Asp Lys Thr Glu Ile Pro Thr Ile Asn Thr Ile Ala Ser Gly Glu Pro Thr Ser Thr Pro Thr Thr Glu Ala Val Glu Ser Thr Val Ala Thr Leu Glu Asp Ser(P) Pro Glu Val Ile Glu Ser Pro Pro Glu Ile Asn Thr Val Gln Val Thr Ser Thr Ala Val (SEQ ID NO: 5) |
| Ser(P)$^{127}$, Ser(P)$^{149}$ κ-casein A (106-169) | Met Ala Ile Pro Pro Lys Lys Asn Gln Asp Lys Thr Glu Ile Pro Thr Ile Asn Thr Ile Ala Ser(P) Gly Glu Pro Thr Ser Thr Pro Thr Thr Glu Ala Val Glu Ser Thr Val Ala Thr Leu Glu Asp Ser(P) Pro Glu Val Ile Glu Ser Pro Pro Glu Ile Asn Thr Val Gln Val Thr Ser Thr Ala Val (SEQ ID NO: 6) |
| Ser(P)$^{149}$ κ-casein B (117-169) | Thr Glu Ile Pro Thr Ile Asn Thr Ile Ala Ser Gly Glu Pro Thr Ser Thr Pro Thr Ile Glu Ala Val Glu Ser Thr Val Ala Thr Leu Glu Ala Ser(P) Pro Glu Val Ile Glu Ser Pro Pro Glu Ile Asn Thr Val Gln Val Thr Ser Thr Ala Val (SEQ ID NO: 7) |
| Ser(P)$^{127}$, Ser(P)$^{149}$ κ-casein B (117-169) | Thr Glu Ile Pro Thr Ile Asn Thr Ile Ala Ser(P) Gly Glu Pro Thr Ser Thr Pro Thr Ile Glu Ala Val Glu Ser Thr Val Ala Thr Leu Glu Ala Ser(P) Pro Glu Val Ile Glu Ser Pro Pro Glu Ile Asn Thr Val Gln Val Thr Ser Thr Ala Val (SEQ ID NO: 8) |
| Ser(P)$^{149}$ κ-casein A (117-169) | Thr Glu Ile Pro Thr Ile Asn Thr Ile Ala Ser Gly Glu Pro Thr Ser Thr Pro Thr Thr Glu Ala Val Glu Ser Thr Val Ala Thr Leu Glu Asp Ser(P) Pro Glu Val Ile Glu Ser Pro Pro Glu Ile Asn Thr Val Gln Val Thr Ser Thr Ala Val (SEQ ID NO: 9) |
| Ser(P)$^{127}$, Ser(P)$^{149}$ κ-casein A (117-169) | Thr Glu Ile Pro Thr Ile Asn Thr Ile Ala Ser(P) Gly Glu Pro Thr Ser Thr Pro Thr Thr Glu Ala Val Glu Ser Thr Val Ala Thr Leu Glu Asp Ser(P) Pro Glu Val Ile Glu Ser Pro Pro Glu Ile Asn Thr Val Gln Val Thr Ser Thr Ala Val (SEQ ID NO: 10) |
| Ser(P)$^{149}$ κ-casein B (138-158) | Ala Val Glu Ser Thr Val Ala Thr Leu Glu Ala Ser(P) Pro Glu Val Ile Glu Ser Pro Pro (SEQ ID NO: 1) |

TABLE 1-continued

Casein Antimicrobial Peptides

| Peptide | Sequence*a* |
|---|---|
| Ser(P)[149] κ-casein A (138-158) | Ala Val Glu Ser Thr Val Ala Thr Leu Glu Asp Ser(P) Pro Glu Val Ile Glu Ser Pro Pro (SEQ ID NO: 2) |

The peptide κ-casein (106-169) is present in cheese whey or rennet whey in several different forms. The peptide has two major genetic variants (A and B) and is post-translationally modified by glycosylation and phosphorylation. The glycosylated forms, known as the Kappa-caseino-glycopeptide or glycomacropeptide have been described by Neeser [U.S. Pat. Nos. 4,992,420 and 4,994,441] as anti-plaque and anti-caries agents by virtue of the oligosaccharide chains linked to threonine residues of the peptide. Neeser claims that the oligosaccharide chains of the glycopeptide, by specifically binding to plaque-forming oral bacteria, block the adherence of these bacteria onto salivary-coated tooth enamel. The glycosylated forms of κ-casein (106-169) can be separated from the non-glycosylated forms by chromatography (eg. anion exchange and reversed-phase HPLC) or by selective precipitation or ultrafiltration. Only the non-glycosylated forms of κ-casein (117-169) or κ-casein (106-169) showed antimicrobial activity. As glycosylation destroys antimicrobial activity it is desirable to separate the glyco- and aglyco-forms of κ-casein (117-169) or κ-casein (106-169) which can be achieved using chromatography, selective precipitation or ultrafiltration. Phosphorylation of Ser[149] and to a lesser extent Ser[127] are important for antimicrobial activity and the phosphorylated forms of the two major genetic variants (A and B) appear to possess equal activity [Table 1]. The Neeser patents do not disclose the antimicrobial activity of κ-casein(106-169) nor the use of the non-glycosylated forms of the peptide for the suppression of bacterial pathogens.

In a particularly preferred embodiment of the invention, the antimicrobial composition is incorporated into dentifrices such as toothpaste, mouth washes or formulations for the mouth to aid in the prevention and/or treatment of dental caries and periodontal diseases. The peptide may comprise 0.01-50% by weight of the dentifrice composition, preferably 0.1-10%. For oral compositions it is preferred that the amount of the composition of the present invention administered is 0.01-50% by weight, preferably 0.1-10% by weight of the composition. The oral composition of this invention which contains the above-mentioned peptides may be prepared and used in various forms applicable to the mouth such as dentifrice including toothpastes, toothpowders and liquid dentifrices, mouthwashes, troches, chewing gums, dental pastes, gingival massage creams, gargle tablets, lozenges, dairy products and other foodstuffs. The oral composition according to this invention may further include additional well known ingredients depending on the type and form of a particular oral composition.

In certain highly preferred forms of the invention the oral composition may be substantially liquid in character, such as a mouthwash or rinse. In such a preparation the vehicle is typically a water-alcohol mixture desirably including a humectant as described below.

Generally, the weight ratio of water to alcohol is in the range of from about 1:1 to about 20:1. The total amount of water-alcohol mixture in this type of preparation is typically in the range of from about 70 to about 99.9% by weight of the preparation. The alcohol is typically ethanol or isopropanol. Ethanol is preferred.

The pH of such liquid and other preparations of the invention is generally in the range of from about 4.5 to about 9 and typically from about 5.5 to 8. The pH is preferably in the range of from about 6 to about 8.0, preferably 7.4. The pH can be controlled with acid (e.g. citric acid or benzoic acid) or base (e.g. sodium hydroxide) or buffered (as with sodium citrate, benzoate, carbonate, or bicarbonate, disodium hydrogen phosphate, sodium dihydrogen phosphate, etc).

Other desirable forms of this invention, the oral composition may be substantially solid or pasty in character, such as toothpowder, a dental tablet or a dentifrice, that is a toothpaste (dental cream) or gel dentifrice. The vehicle of such solid or pasty oral preparations generally contains dentally acceptable polishing material. Examples of polishing materials are water-insoluble sodium metaphosphate, potassium metaphosphate, tricalcium phosphate, dihydrated calcium phosphate, anhydrous dicalcium phosphate, calcium pyrophosphate, magnesium orthophosphate, trimagnesium phosphate, calcium carbonate, hydrated alumina, calcined alumina, aluminium silicate, zirconium silicate, silica, bentonite, and mixtures thereof. Other suitable polishing material include the particulate thermosetting resins such as melamine-, phenolic, and urea-formaldehydes, and cross-linked polyepoxides and polyesters. Preferred polishing materials include crystalline silica having particle sized of up to about 5 microns, a mean particle size of up to about 1.1 microns, and a surface area of up to about 50,000 $cm^2$/gm., silica gel or colloidal silica, and complex amorphous alkali metal aluminosilicate.

When visually clear gels are employed, a polishing agent of colloidal silica, such as those sold under the trademark SYLOID as Syloid 72 and Syloid 74 or under the trademark SANTOCEL as Santocel 100, alkali metal alumino-silicate complexes are particularly useful since they have refractive indices close to the refractive indices of gelling agent-liquid (including water and/or humectant) systems commonly used in dentifrices.

Many of the so-called "water insoluble" polishing materials are anionic in character and also include small amounts of soluble material. Thus, insoluble sodium metaphosphate may be formed in any suitable manner as illustrated by Thorpe's Dictionary of Applied Chemistry, Volume 9, 4th Edition, pp. 510-511. The forms of insoluble sodium metaphosphate known as Madrell's salt and Kurrol's salt are further examples of suitable materials. These metaphosphate salts exhibit only a minute solubility in water, and therefore are commonly referred to as insoluble metaphosphates (IMP). There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, may be reduced or eliminated by washing with water if desired. The insoluble alkali metal metaphosphate is typically employed in powder form of a particle size such that no more than 1% of the material is larger than 37 microns.

The polishing material is generally present in the solid or pasty compositions in weight concentrations of about 10% to about 99%. Preferably, it is present in amounts from about 10% to about 75% in toothpaste, and from about 70% to about 99% in toothpowder. In toothpastes, when the polishing material is silicious in nature, it is generally present in amount of about 10-30% by weight. Other polishing materials are typically present in amount of about 30-75% by weight.

In a toothpaste, the liquid vehicle may comprise water and humectant typically in an amount ranging from about 10% to about 80% by weight of the preparation. Glycerine, propylene glycol, sorbitol and polypropylene glycol exemplify suitable humectants/carriers. Also advantageous are liquid mixtures of water, glycerine and sorbitol. In clear gels where the refractive index is an important consideration, about 2.5-30% w/w of water, 0 to about 70% w/w of glycerine and about 20-80% w/w of sorbitol are preferably employed.

Toothpaste, creams and gels typically contain a natural or synthetic thickener or gelling agent in proportions of about 0.1 to about 10, preferably about 0.5 to about 5% w/w. A suitable thickener is synthetic hectorite, a synthetic colloidal magnesium alkali metal silicate complex clay available for example as Laponite (e.g. CP, SP 2002, D) marketed by Laporte Industries Limited. Laponite D is, approximately by weight 58.00% $SiO_2$, 25.40% MgO, 3.05% $Na_2O$, 0.98% $Li_2O$, and some water and trace metals. Its true specific gravity is 2.53 and it has an apparent bulk density of 1.0 g/ml at 8% moisture.

Other suitable thickeners include Irish moss, iota carrageenan, gum tragacanth, starch, polyvinylpyrrolidone, hydroxyethylpropylcellulose, hydroxybutyl methyl cellulose, hydroxypropyl methyl cellulose, hydroxyethyl cellulose (e.g. available as Natrosol), sodium carboxymethyl cellulose, and colloidal silica such as finely ground Syloid (e.g. 244). Solubilizing agents may also be included such as humectant polyols such propylene glycol, dipropylene glycol and hexylene glycol, cellosolves such as methyl cellosolve and ethyl cellosolve, vegetable oils and waxes containing at least about 12 carbons in a straight chain such as olive oil, castor oil and petrolatum and esters such as amyl acetate, ethyl acetate and benzyl benzoate.

It will be understood that, as is conventional, the oral preparations are to be sold or otherwise distributed in suitable labelled packages. Thus, a jar of mouthrinse will have a label describing it, in substance, as a mouthrinse or mouthwash and having directions for its use; and a toothpaste, cream or gel will usually be in a collapsible tube, typically aluminium, lined lead or plastic, or other squeeze, pump or pressurized dispenser for metering out the contents, having a label describing it, in substance, as a toothpaste, gel or dental cream.

Organic surface-active agents are used in the compositions of the present invention to achieve increased prophylactic action, assist in achieving thorough and complete dispersion of the active agent throughout the oral cavity, and render the instant compositions more cosmetically acceptable. The organic surface-active material is preferably anionic, non-ionic or ampholytic in nature which does not denature the antimicrobial peptide of the invention, and it is preferred to employ as the surface-active agent a detersive material which imparts to the composition detersive and foaming properties while not denaturing the peptide. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkylsulfo-acetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material. The use of these sarconite compounds in the oral compositions of the present invention is particularly advantageous since these materials exhibit a prolonged marked effect in the inhibition of acid formation in the oral cavity due to carbohydrates breakdown in addition to exerting some reduction in the solubility of tooth enamel in acid solutions. Examples of water-soluble nonionic surfactants suitable for use with peptides are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides, polyhydric alcohols (e.g. sorbitan monostearate) and polypropyleneoxide (e.g. Pluronic materials).

Surface active agent is typically present in amount of about 0.1-5% by weight. It is noteworthy, that the surface active agent may assist in the dissolving of the peptide of the invention and thereby diminish the amount of solubilizing humectant needed.

Various other materials may be incorporated in the oral preparations of this invention such as whitening agents, preservatives, silicones, chlorophyll compounds and/or ammoniated material such as urea, diammonium phosphate, and mixtures thereof. These adjuvants, where present, are incorporated in the preparations in amounts which do not substantially adversely affect the properties and characteristics desired.

Any suitable flavouring or sweetening material may also be employed. Examples of suitable flavouring constituents are flavouring oils, e.g. oil of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, xylitol, sodium cyclamate, perillartine, AMP (aspartyl phenyl alanine, methyl ester), saccharine, and the like. Suitably, flavour and sweetening agents may each or together comprise from about 0.1% to 5% more of the preparation.

In the preferred practice of this invention an oral composition according to this invention such as mouthwash or dentifrice containing the composition of the present invention is preferably applied regularly to the gums and teeth, such as every day or every second or third day or preferably from 1 to 3 times daily, at a pH of about 4.5 to about 9, generally about 5.5 to about 8, preferably about 6 to 8, for at least 2 weeks up to 8 weeks or more up to a lifetime.

The compositions of this invention can be incorporated in lozenges, or in chewing gum or other products, e.g. by stirring into a warm gum base or coating the outer surface of a gum base, illustrative of which may be mentioned jelutong, rubber latex, vinylite resins, etc., desirably with conventional plasticisers or softeners, sugar or other sweeteners or such as glucose, sorbitol and the like.

In another embodiment, the composition of the invention is formulated in foods to act as a preservative preferably comprising 0.01-10% w/w, more preferably 0.1-5% w/w, most preferably 1-5% and particularly 2% w/w.

The present invention provides compositions including pharmaceutical compositions comprising the divalent cation and the peptide as described together with a pharmaceutically-acceptable carrier. Such compositions may be selected from the group consisting of dental, intra-oral compositions, therapeutic anti-infective compositions for topical and systemic application. Dental compositions or therapeutic compositions rnay be in the form of a gel, liquid, solid, powder, cream or lozenge. Therapeutic compositions may also be in the form of tablets or capsules.

The present invention also provides a method of treating or preventing dental caries or periodontal disease comprising the step of administering the composition of the invention to the teeth or gums of a subject in need of such treatments. Topical administration of the composition is preferred.

It will be clearly understood that, although this specification refers specifically to applications in humans, the invention is also useful for veterinary purposes. Thus in all aspects the invention is useful for domestic animals such as cattle, sheep, horses and poultry; for companion animals such as cats and dogs; and for zoo animals.

In order that the nature of the present invention may be more clearly understood preferred forms thereof will now be described with reference to the following non-limiting examples.

FIGURE LEGENDS

FIG. 1: Chromatogram of purified Ser(P)$^{149}$κ-casein-B (138-158). A sample of the purified peptide fraction was applied to a RP-HPLC analytical column. Purified peptide was eluted from the column using a linear gradient of 0-100% buffer B (30 min). The flow rate was 1 mL/min. Buffer A was 0.1% acetic acid in water, pH 5.5 (TEA) and buffer B was 60% acetonitrile containing 0.1% acetic acid in water, pH 5.5 (TEA).

Figure 2:
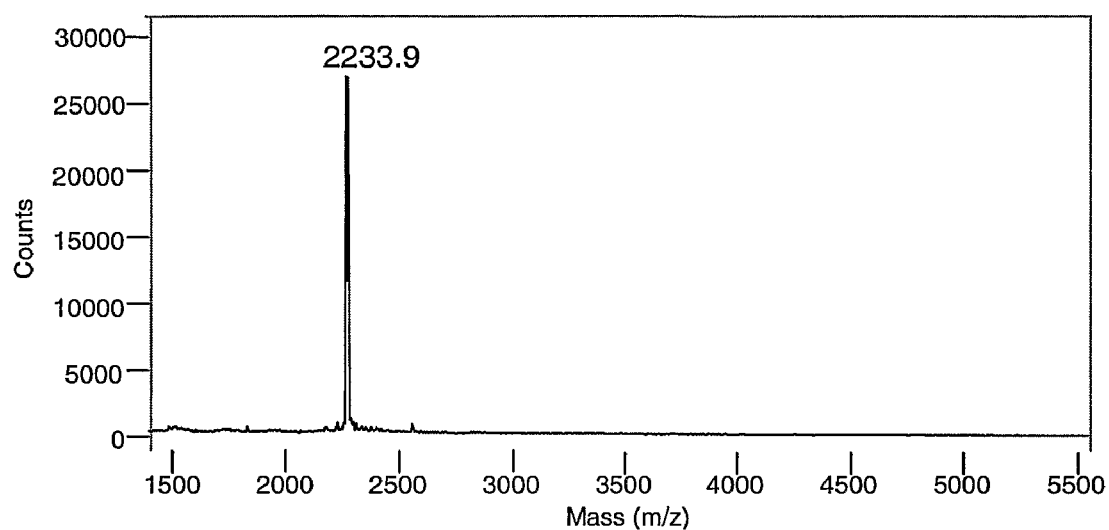

FIG. 2: Mass spectrometric analysis of RP-HPLC fraction B using the MALDI-TOF MS. The major peak observed with a MW of 2233.9 Da corresponded to the synthesised peptide, Ser(P)$^{149}$ κ-casein-B(138-158). Spectrum was obtained in linear, negative mode with an accelerating voltage of 20 kV, grid voltage of 93% and pulse delay time of 100 ns.

Figure 3:
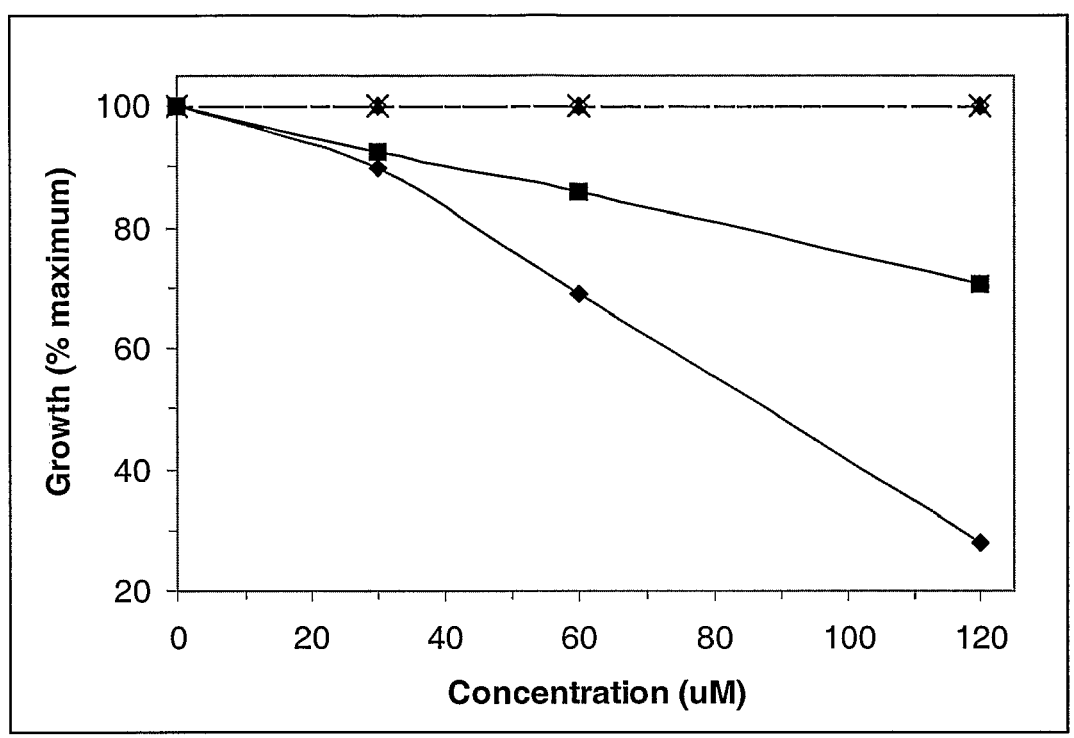

FIG. 3. Effect of κ-casein-A(106-169) [▲]; κ-casein-B (106-169) [◇]; ZnCl$_2$ [X]; Zn:κ-casein-B(106-169) in a 1:1 ratio [■] and Zn:κ-casein-A(106-169) in a 1:1 ratio [♦] on *Streptococcus mutans* growth in THYE at pH 7.2.

Figure 4:
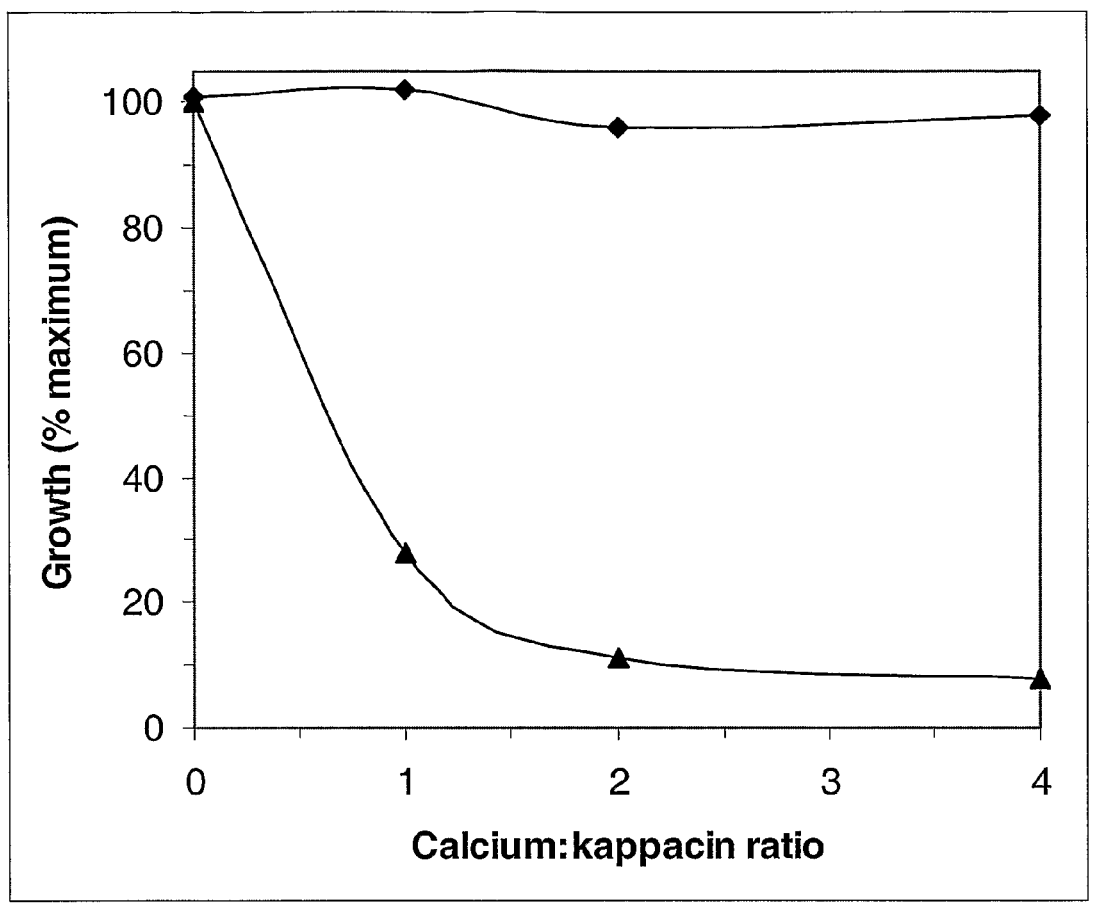

FIG. 4. Effect of calcium ion concentration on the growth inhibitory activity of 250 µM κ-casein-A(106-169) tested against *S. mutans* at pH 7.2. CaCl$_2$ control (♦); Ca:κ-casein-A(106-169) (▲). κ-casein-A(106-169) was incubated with CaCl$_2$ at ratios between 1:0 and 1:4 for 1 h prior to addition to the assay.

Figure 5:
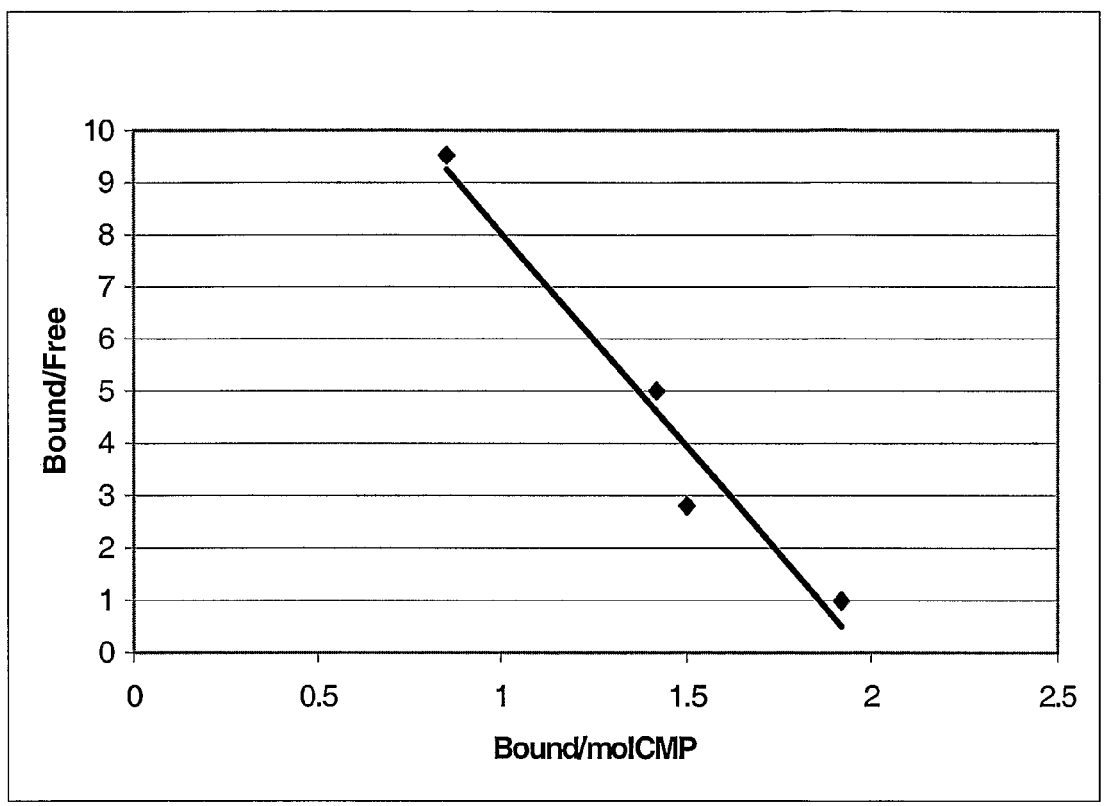

FIG. 5. Scatchard analysis of zinc binding to κ-casein-A (106-169). ZnCl$_2$ was incubated with purified κ-casein-A (106-169) in water at pH 7.3 for 1 h at 37° C. Samples were then centrifuged through 3,000 molecular weight cut-off filtration membranes. The amount of zinc ions was determined by atomic absorption spectrometry.

Figure 6:
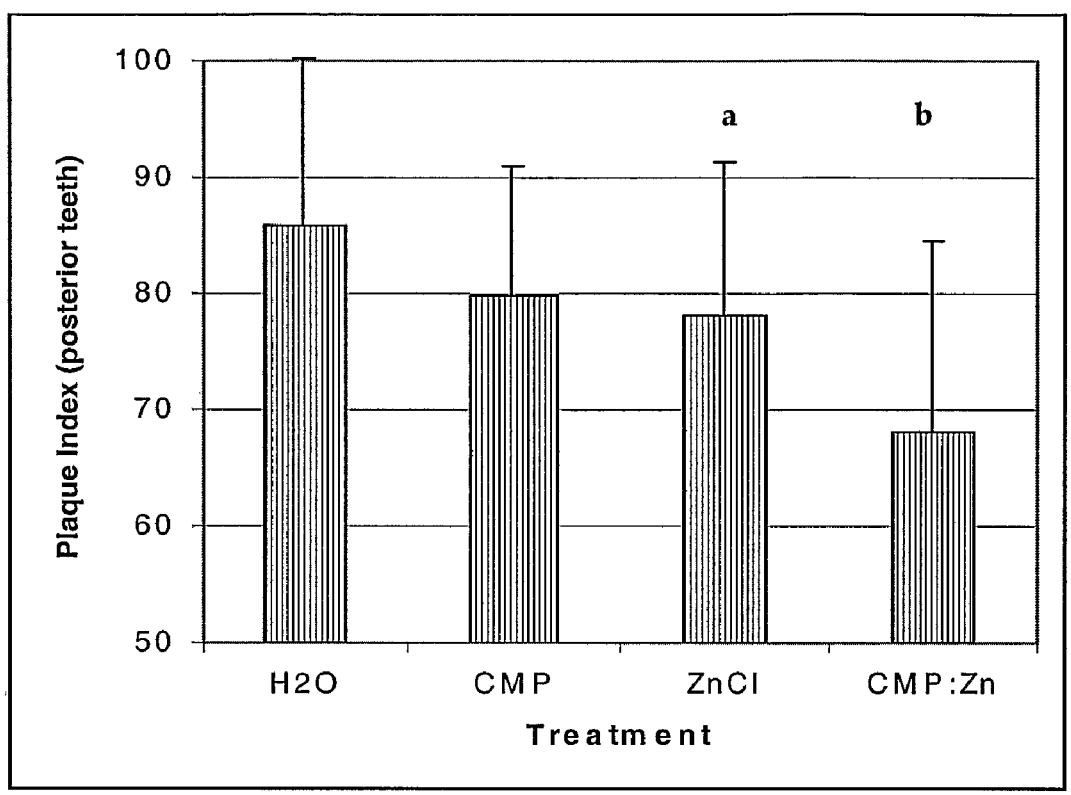

FIG. 6 Effect of Kappacin (10 mg/ml), ZnCl$_2$ (20 mM) and Kappacin:ZnCl$_2$ when used as mouthrinses as the only form of oral hygiene on the mean plaque index scores for posterior teeth. a=significantly different from water control; b=significantly different from all other treatments; as determined using the Wilcoxon rank test.

Figure 7:
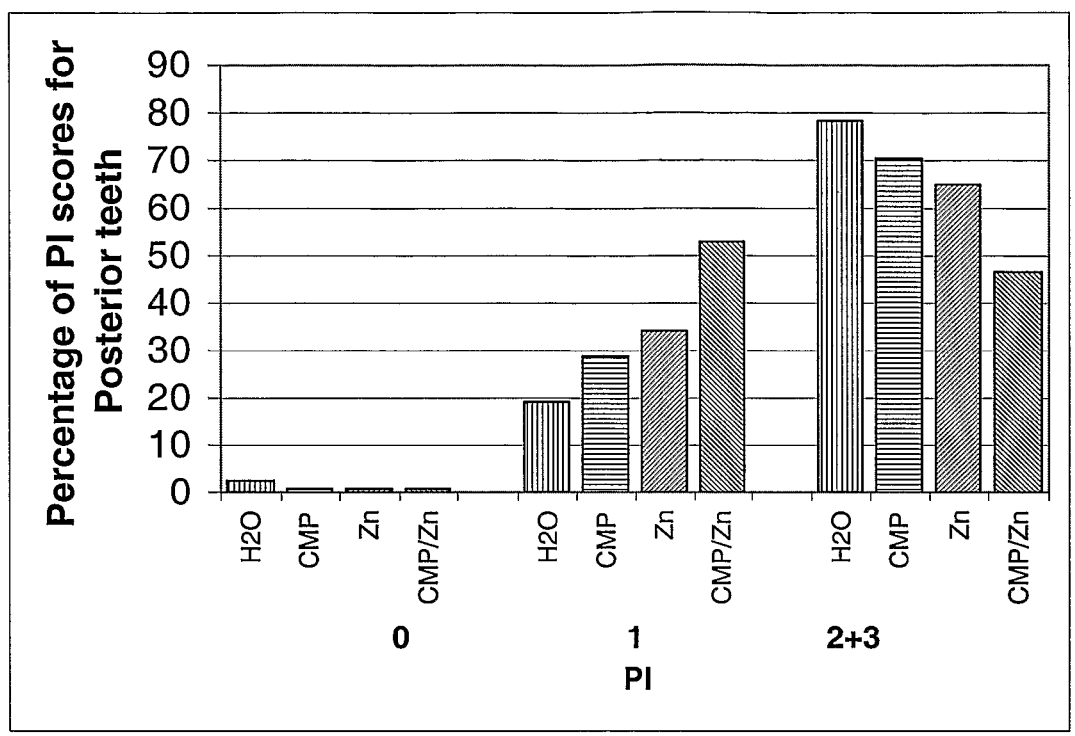

FIG. 7. Effect of mouthrinses on distribution of plaque index scores of posterior teeth.

In order that the nature of the present invention may more readily understood preferred forms thereof will now be described with reference to the following Examples.

MATERIALS AND METHODS

Kappacin Preparation

Caseinate-HCl (Bonlac Foods, Melbourne Australia) was dissolved by slow addition with constant stirring to deionised water at 50° C., pH 8.0 to give a final concentration of 21.5 g/L. Once the caseinate had dissolved, the temperature was lowered to 37° C. and the pH adjusted to 6.3 by the slow addition of 1 M HCl to avoid precipitation of casein. To begin the hydrolysis Rennet (90% Chymosin EC 3.4.23.4, 145 IMCU/ml, Single Strength, Chr. Hanson) was added to a final concentration of 1.2 IMCU/g casein and the solution stirred at 37° C. for 1 h. The pH of the solution was maintained at 6.3±0.2 by the addition of 1 M HCl and 1 M NaOH. Hydrolysis was stopped by the addition of trichloroacetic acid to a final concentration of 4% and the precipitated proteins were pelleted by centrifugation (5,000 g, 15 min, 4° C.). The supernatant containing the caseinomacropeptide (CMP) was concentrated by diafiltration using a 3000 Da cutoff membrane (S10Y3, Amicon). This material was then lyophilized. This preparation was further fractionated into glycosylated forms, non-glycosylated κ-casein-A(106-169) and nonglycosylated κ-casein-B(106-169) by reversed phase HPLC using a C$_{18}$ column and elution with 90% acetonitrile/0.1% v/v TFA, as described previously (Malkoski et al., 2001). The eluant was monitored using a primary wavelength of 215 nm. The identity of each fraction was confirmed by mass spectrometric analysis using a Voyager linear matrix assisted laser desorption/ionisation time of flight mass spectrometer (MALDI MS; PerSeptive Biosystems, MA, USA) and N-terminal sequence analysis as described previously (Malkoski et al., 2001).

Solid Phase Peptide Synthesis and Purification

Peptides corresponding to Ser(P)$^{149}$κ-casein-A(138-158) and Ser(P)$^{149}$κ-casein-B(138-158) were synthesized using standard solid phase peptide synthesis protocols as described previously (Malkoski et al., 2001). Peptides were purified by reversed phase HPLC using a C$_{18}$ column and identified by mass spectrometric analysis as described previously (Malkoski et al., 2001).

Antibacterial Planktonic Assay

The oral opportunistic pathogen *Streptococcus mutans* Ingbritt was used in this study as an indicator strain. The antibacterial assay was conducted in 96 well plates and bacterial growth continuously monitored over 40 h, as previously described (Malkoski et al., 2001). Briefly, bacteria were cultured in Todd Hewitt Broth (36.4 g/l) containing Yeast extract (5.0 g/l) and 100 mM potassium phosphate with a pH of 6.3 or 7.2. The bacterial inocula were prepared by diluting exponentially growing cells in growth medium to give 2.7×10$^4$ viable cells/ml. In the bacterial growth assays test wells contained κ-casein-A(106-169) or κ-casein-B(106-169) at concentrations between 20 and 120 µM. these peptides were also tested in combination with zinc or calcium ions to give ratios of Kappacin:divalent metal ion of 1:1 to 1:4. Synthetic Ser(P) $^{149}$κ-casein-A(138-158) and Ser(P)$^{149}$κ-casein-B(138-158) peptides were also tested in this assay. The plates were incubated at 37° C. and growth determined by measuring optical density (OD) at 620 nm using an iEMS microplate reader (Labsystems, OY Research Technologies Division).

Biofilm Growth of *S. mutans*.

A constant depth film fermenter (CDFF: Wimmpenny, Cardiff University, UK) was used for biofilm formation. The CDFF consists of a stainless steel disc rotating at a constant speed of 3 rpm containing 15 polytetrafluoroethylene (PTFE) pans each of which contain 5 plugs of 4.5 mm in diameter. The plugs were set to 0.4 mm below the surface of the steel disc. Inbuilt scrapers were used to maintain a constant biofilm depth of 0.4 mm. The scrapers are attached so that the stainless steel disc rotates under them; the scrapers are spring loaded so that they are pressed down against the pans. An anaerobic atmosphere was maintained in the CDFF by continuous gassing with 5% $CO_2$ in $N_2$. The CDFF was housed in a modified $CO_2$ incubator, which was used to maintain a constant culture temperature of 37° C. A *S. mutans* Ingbritt batch culture in Todd Hewitt (35.4 g/l), Yeast Extract (8 g/L) broth (THYE) in exponential growth phase was used to inoculate the CDFF at a flow rate of 30 ml/h for 5 h. The growth media, THYE containing 0.1% (w/v) sucrose, was then pumped into the CDFF at a constant flow rate of 40 ml/h.

At specified times prior to and after treatment with solutions, plugs were removed from the CDFF, washed to remove planktonic bacteria and viable counts were performed to determine bacterial numbers. To assess the effect on cell viability of various solutions growth media addition to the CDFF was suspended for 10 min and replaced by the solution at a flow rate of 30 ml/h. After 10 min growth media addition was resumed. Solutions tested in the CDFF were: 2 mM Tris-HCl pH6.0; 10 mg/ml Kappacin preparation (see above) in 2 mM Tris-HCl pH 6.0; 10 mg/ml Kappacin preparation (see above) and 20 mM $ZnCl_2$ in 2 mM Tris-HCl pH 6.0; 20 mM $ZnCl_2$ in 2 mM Tris-HCl pH 6.0; 2 mM $ZnCl_2$ in 2 mM Tris-HCl pH 6.0 and 0.05% chlorhexidine digluconate in deionized water.

Divalent Metal Cation Binding Assay $CaCl_2$ or $ZnCl_2$ at specified concentrations between 135 and 540 μM was incubated with purified κ-casein-A(106-169) at a concentration of 135 μM in water at pH 7.3 for 1 h at 37° C. with stirring. Samples were then centrifuged (1,000 g, 10 min) through 3,000 Da cut-off filtration membranes (YM3 Cellulose, Millipore Bedford Mass., USA) to separate unbound divalent cations from the peptide with bound cations. The amount of calcium or zinc ions in the filtrate and initial sample was then determined by atomic absorption spectrometry (Model 373 AAS, Perkin-Elmer) set on absorption mode at 422.7 nm or 213.9 nm, respectively. The total amount of zinc or calcium in the sample and free (unbound) zinc or calcium was calculated by reference to a standard curve. Binding to κ-casein-A(106-169) was determined by Scatchard analysis.

Structural Determination

One dimensional $^1H$ NMR spectra of synthetic $Ser(P)^{149}$κ-casein-A(138-158) were acquired on a Varian Unity Inova spectrometer (Palo Alto, Calif., USA) operating at 600 MHz. A series of spectra were recorded at a constant pH of 6.5 with trifluoroethanol (TFE) concentrations of 0, 5, 15 and 30% (v/v) and an initial peptide concentration of 3 mM. The pH was adjusted by dropwise addition of 1 M HCl. A spectrum was recorded with a final peptide concentration of 2.3 mM in 30% TFE and 3 mM $CaCl_2$. All spectra were recorded at a probe temperature of 5° C. Solvent suppression was achieved through the use of the WET-1D sequence (Smallcombe et al., 1995).

Clinical Trial

Ten subjects were recruited for the double-blind, cross-over study. Subjects were recruited from undergraduate students enrolled at the School of Dental Science, The University of Melbourne. The group consisted of 6 females and 4 males with a mean age of 21 years. Subjects were examined prior to the commencement of the trial and all were gauged to be of good health, having dentitions without unrestored carious lesions or evidence of moderate to severe gingivitis. The subjects had not used any dentifrices containing antimicrobial agents prior to commencement of the trial. Approval was obtained from the Human Research Ethics Committee of the University of Melbourne.

At the commencement of the trial, the subjects were instructed to cease all other forms of daily oral hygiene practices and to solely rely on the use of the allocated mouthrinse solution. Four solutions were tested as mouthrinses in this investigation: Solution A: Deionized water. B: 1% (w/v) Kappacin preparation in deionized water. C: 20 mM ZnCl in deionized water. D: 1% (w/v) Kappacin preparation and 20 mM ZnCl in deionized water. The pH of all solutions was adjusted to 6.9±0.1 using KOH. Subjects were instructed to rinse three times daily: morning, mid-day and evening with 15 ml of solution for a duration of one minute. Each trial session was for four days with a clinical evaluation at the end of the trial. The Silness and Loe Plaque Index (PI) was used to evaluate plaque (Silness and Loe, 1964). The gingival area of each tooth surface (distal, buccal, mesial and lingual) was given a score from 0-3. All teeth excluding third molars were scored at the conclusion of the trial. Following each trial session the subjects resumed their normal oral hygiene habits for a minimum of seven days prior to the next trial. Data were analysed using the nonparametric Wilcoxon rank test.

Results.

Antibacterial Activity of the Genetic Variants of κ-Casein (106-169).

To determine whether the difference in the relative antibacterial activities of the two major genetic variants of Kappacin [κ-casein(106-169)] activity was due to the amino acid sequence difference in the previously identified active region of κ-casein-A(106-169), residues 138-158, $Ser(P)^{149}$κ-casein-B(138-158) was synthesized and its activity tested. The purity of the synthetic $Ser(P)^{149}$κ-casein-B(138-158) was determined by reversed-phase HPLC and a single peak was observed (FIG. 1). Analysis of this peak by mass spectrometry gave a single peak with an observed mass (m/z) of 2233.9 Da which corresponded to the calculated mass for the synthetic peptide, $Ser(P)^{149}$κ-casein-B(138-158) of 2235.4 (FIG. 2). The calculated MIC for the synthetic peptide Ser(P) $^{149}$κ-casein-B(138-158) tested against *S. mutans* at a growth pH of 6.28 in the microplate growth assay was 44 μM.

Interaction of Kappacin with Divalent Metal Cations.

There was no inhibition of *S. mutans* growth by either of the synthetic active region peptides [$Ser(P)^{149}$κ-casein-A(138-158) and $Ser(P)^{149}$κ-casein-B(138-158)] or the genetic variants of the purified full length peptides when tested at a growth pH of 7.20 up to concentrations of 300 μM. When the two genetic variants of κ-casein(106-169) were tested for bacterial growth inhibitory activity at pH 7.20 in the presence of an equimolar concentration of the antibacterial divalent cation $Zn^{2+}$ a synergistic effect was observed (FIG. 3). Zinc ions alone had a MIC of 200 μM, which masked the synergistic effect of Kappacin and zinc when tested at ratios above 1:1. Interestingly when the zinc ions were replaced with calcium ions an antibacterial effect was detectable with κ-casein-A(106-169) although no effect on *S. mutans* growth could be detected with κ-casein-B(106-169) and calcium in a 1:1 ratio up to 300 μM (Table 2).

The optimal ratio of calcium to κ-casein-A(106-169) for bioactivity was determined by testing various ratios against *S. mutans* in the microplate growth assay. A ratio of 2:1 was shown to be more effect than 1:1, whilst increasing the calcium:κ-casein-A(106-169) ratio to 4:1 did not increase activity (FIG. 4).

Scatchard analysis of binding assays using κ-casein-A (106-169) with the divalent cation $Zn^{2+}$ demonstrated that there were two binding sites for zinc in this peptide (FIG. 5). Similar results were obtained for calcium binding.

TABLE 2

Minimal Inhibitory Concentrations of the two genetic variants of non-glycosylated, phosphorylated, κ-casein(106-169) and the synthetic peptide Ser(P)[149]κ-casein-A(138-158) tested singly and in combination with a 1:1 ratio of zinc or calcium against *S. mutans* at pH 7.20.

|  | MIC (μM) |
| --- | --- |
| κ-casein-A(106-169) | NI* |
| κ-casein-B(106-169) | NI |
| κ-casein-A(106-169) and Calcium | 248 |
| κ-casein-B(106-169) and Calcium | NI |
| κ-casein-A(106-169) and Zinc | 161 |
| κ-casein-B(106-169) and Zinc | 200 |
| Ser(P)[149]κ-casein-A(138-158) and Zinc | 149 |
| Ser(P)[149]κ-casein-A(138-158) | NI |
| $ZnCl_2$ | 200 |
| $CaCl_2$ | NI |

*No inhibition at concentrations up to 1 mM

Effect of Kappacin and Zinc on the Viability of *Streptococcus mutans* Cultured as a Biofilm.

After inoculation into the CDFF biofilm fermenter *S. mutans* rapidly formed a stable biofilm that contained 5-6× $10^8$ viable cells per plug. Addition of 5 ml of 2 mM Tris-HCl pH 6.0 had little effect on the viable count of *S. mutans* in the biofilm. In contrast addition of 5 ml of a 1% (w/v) Kappacin preparation in 2 mM Tris-HCl pH 6.0 resulted in a rapid decrease in the *S. mutans* viable cell count such that 2 h after addition there had been a 99.5% reduction in the viable count. Recovery of the *S. mutans* biofilm was slow after Kappacin addition and 3 days after the addition bacterial counts were still less than 13% of the pretreatment level. Addition of 5 ml of 2 mM $ZnCl_2$ in 2 mM Tris-HCl pH 6.0 to a stable biofilm of *S. mutans* in the CDFF reduced the viable count by ~60%. The number of viable cells rapidly recovered from this treatment. The addition of 20 mM $ZnCl_2$ to the biofilm in an identical manner resulted in a decrease in viable cell counts of 92% Again a rapid recovery of viable cell counts was observed. The addition of Kappacin:zinc (1% w/v Kappacin, 20 mM Zn) to a *S. mutans* biofilm caused a rapid decrease in viable cell numbers, with a 96.0% decrease in 2 h. However, three days after the kappacin:zinc treatment the number of viable *S. mutans* in the biofilm had decreased to less than 0.5% of pretreatment levels. Further, the viability of *S. mutans* in the biofilm did not recover from the Kappacin:zinc treatment over the following 15 days. To test the comparative efficacy of Kappacin and Kappacin:zinc a 0.05% (w/v) solution of chlorhexidine digluconate was tested against *S. mutans* in the CDFF biofilm fermenter. A decrease in *S. mutans* cell viability of 48% was seen with a rapid recovery of cell viability such that 3.5 hour after treatment there was no significant difference to pre-treatment viability.

Structural Analysis.

The amide region of a $^1H$ NMR spectrum of synthetic Ser(P)[149]κ-casein-A(138-158) recorded in 90% $H_2O$/10% $D_2O$ solution shows that the amide resonances are not well dispersed, occurring in a 0.6 ppm region extending from about δ8.15 to δ8.75. This is characteristic of peptides in a 'random-coil' conformation. Addition of 5% (v/v) TFE resulted in a change of chemical shift for some of the resonances and a general broadening of the peaks. The broadening of the peaks is a result of chemical exchange in which peptide molecules exist in two environments, the aqueous solution or the more apolar environment of the TFE micelles. The peptide molecules exchange their environments at a rate comparable to the difference in amide chemical shift in the two environments. As more TFE was added to the sample the peptide became preferentially associated with the apolar TFE environment and the rate of exchange with the aqueous phase slowed. These changes are associated with further changes in amide chemical shifts and a general sharpening of the NMR resonances. However, the range of chemical shifts is still relatively small with a range of 0.6 ppm from about δ8.1 to δ8.7 indicating that the peptides are still in a 'random-coil' conformation. The addition of a molar excess of calcium ions resulted in the amide resonances spreading over a range of 1.25 ppm from δ7.75 to δ9.0, a range characteristic of a peptide in a specific conformation.

Clinical Trial.

A commercial preparation of Kappacin-enriched CMP was used in a double-bind, cross over, small-scale clinical anti-plaque trial involving 10 subjects. HPLC analysis of the preparation indicated that in a 10.0 mg/ml solution there was 4.4 mg/ml of nonglycosylated κ-casein-A(106-169), 1.9 mg/ml of nonglycosylated κ-casein-B(106-169) and 3.0 mg/ml of glycosylated κ-casein(106-169). Based on a calculated average molecular weight for glycosylated κ-casein (106-169) of 7500, there was a concentration of ~1.33 mM of all forms of κ-casein(106-169) in the preparation, therefore there was a Zn:CMP ratio of ~15:1.

After four days with the water (control) mouthrinse as the only form of oral hygiene the mean whole mouth Silness and Loe Plaque Index Score was 178.9±33.5; when only considering the posterior teeth a mean Plaque Index Score of 85.9±14.4 was obtained. Compared with the water control the Kappacin mouthrinse resulted in a decrease in the mean Plaque Index Score of posterior teeth of 7%, the ZnCl mouthrinse caused a 9% decrease whilst the Zn:Kappacin treatment caused a decrease of 21% (FIG. 6). The $ZnCl_2$ mouthrinse significantly (P<0.05) reduced plaque accumulation relative to the water treatment, as determined by a Wilcoxon rank test considering the posterior teeth plaque index scores. The Kappacin mouthrinse was not significantly different to the water control. The Zn:Kappacin mouthrinse significantly (P<0.05) reduced plaque accumulation relative to all other treatments.

The distribution of plaque scores on the posterior teeth also changed with the type of mouthrinse used. The Kappacin:zinc containing mouthrinse resulted in only 47% of surfaces having a plaque index score of 2 or above compared with the water mouthrinse where 78% of tooth surfaces had a score of 2 or more (FIG. 7).

Discussion

The nonglycosylated, phosphorylated forms of the caseinomacropeptide [κ-casein(106-169)], (Kappacin) have been shown to have antibacterial activity against both Gram-negative and Gram-positive oral bacteria at acidic pH. Of the six known genetic variants κ-casein-A(106-169) and κ-casein-B (106-169) are, by far, the most abundant forms. We have previously shown that κ-casein-A(106-169) had better antibacterial activity than κ-casein-B(106-169), that the antibacterial activity of κ-casein-A(106-169) could be localised to residues 138-158 and that phosphorylation of Ser[149] was essential for activity (Malkoski et al., 2001, WO99/26971). To determine if the lower antibacterial activity of κ-casein-B (106-169) was due to the hydrophilic to hydrophobic amino acid substitution within the 138-158 region (Asp[148] in variant A to Ala[148] in variant B) the activity of the synthetic peptide Ser(P)[149]κ-casein-B(138-158) was determined. The MIC for synthetic Ser(P)[149]κ-casein-B(138-158) against S. mutans at pH 6.28 was 44 μM which compared with the previous study showing the MIC of synthetic Ser(P)[149]κ-casein-A(138-158) under identical conditions was 26 μM (Malkoski et al., 2001). Therefore the difference in amino acid sequence of the active region is likely to account for most, if not all, of the difference in activity of the A and B genetic variants of κ-casein(106-169) against S. mutans at pH 6.28.

At neutral pH (7.20) neither of the nonglycosylated, phosphorylated κ-casein(106-169) genetic variants had antibacterial activity against the indicator species S. mutans (Table 2). The addition of the divalent metal cation zinc in a 1:1 ratio with κ-casein-A(106-169) produced an antibacterial effect against S. mutans with an MIC of 161 μM which was lower than that seen for zinc alone (Table 2, FIG. 3). The combination of zinc with κ-casein-B(106-169) in a 1:1 ratio did not produce an MIC that was lower than that for zinc alone, however at sub-MIC levels this combination had some growth inhibitory activity that was not detected with zinc or κ-casein-B(106-169) alone at the same concentrations (FIG. 3). The combination of zinc and the synthetic peptide Ser(P)[149]κ-casein-A(138-158) in a 1:1 ratio had a similar MIC to that seen with zinc:κ-casein-A(106-169), indicating that the divalent metal ions may interact with this region of the peptide. To determine if this enhanced activity at neutral pH was due to the antibacterial activity of zinc or whether it was due to a conformational change in the peptide calcium, a divalent metal cation with no antibacterial activity, was tested with CMP-derived peptides. The addition calcium in a 1:1 ratio with κ-casein-A(106-169) produced an antibacterial effect against S. mutans with an MIC of 248 μM (Table 2). Calcium alone had no effect on S. mutans growth at concentrations up to 1 mM. No antibacterial effect was detected by combining calcium with κ-casein-B(106-169) (Table 2). This suggests that the presence of the divalent metal cation is helping to potentiate the activity of κ-casein-A(106-169) at neutral pH possibly by modifying the structure of the peptide. The most efficacious ratio of divalent metal cation to κ-casein-A(106-169) was determined to be 2:1 using calcium (FIG. 4) which was consistent with the results of Scatchard analysis indicating that κ-casein-A(106-169) specifically binds two divalent metal cations (either calcium or zinc; FIG. 5).

In vivo oral bacteria are found as dental plaque, a biofilm attached to the hard tissues (teeth). S. mutans was grown as a biofilm in a constant depth film fermenter in a growth medium containing free sucrose to more closely simulate conditions found in the oral cavity. To accurately determine the antimicrobial activity of an agent it should be tested in a biofilm model (Wilson, 1996). The constant depth film fermenter provides a sophisticated means of reproducibly producing large numbers of biofilms that can then be used to quantitate the effects of antimicrobial agents that gives predictive results for antiplaque activity (Hope and Wilson, 2003; Shu et al., 2003; Wilson, 1996; Wimpenny et al., 1989). The addition of Kappacin or Kappacin:zinc solutions to the S. mutans biofilm resulted in a dramatic decrease of viable cells. Interestingly this decrease in bacterial cell numbers was sustained for a long period of time, indicating that Kappacin may function more efficiently against biofilm bacteria than planktonic bacteria. In comparison a 0.05% solution of chlorhexidine, a recognised antiplaque additive to mouthrinses, had a lesser effect on S. mutans viability and a less sustained effect.

Kappacin is an unusual antibacterial peptide in that it contains a high proportion of negatively charged amino acids. The Pi of κ-casein-A(106-169) is 3.9 and over the pH range 5 to 8 there is little change in the charge of the molecule, which is approximately −7.

Structural analysis of the synthetic peptide κ-casein-A (138-158) indicated that it will interact with apolar phases, such as the bacterial cell membrane, and that in the presence of excess calcium ions adopts a specific conformation in that environment. These conclusions are consistent with the work of both Smith et al. (2002), who determined the structure of glycosylated and nonglycosylated CMP in the absence of calcium and found it to be largely random, flexible structure, and Plowman, (1997) who found that this region of CMP had a propensity to form an amphipathic α-helix, in the presence of TFE.

A commercial preparation of Kappacin, made from casein, was used in a clinical antiplaque trial. In this preparation the nonglycosylated forms of CMP (Kappacin) accounted for 63% of the dry weight, of which 70% was genetic variant A and 30% was variant B. The Kappacin-zinc combination mouthrinse was significantly more effective in controlling supragingival dental plaque when used as the only oral hygiene procedure than mouthrinses containing Kappacin or zinc alone, suggesting a synergistic effect. Zinc citrate has previously been shown in a double blind crossover trial to significantly reduce the plaque accumulation in subjects by 5-8% using the Turesky plaque index (Addy et al., 1980). The zinc chloride mouthrinse produced similar results in this study, where mean whole mouth plaque index scores, and mean posterior teeth plaque index scores decreased by 6% and 9%, respectively. Giertsen et al. (1988) showed that the use of zinc chloride as a mouthrinse resulted in a significant increase of 9% in the tooth surfaces with no plaque, using the Silness and Loe plaque index, compared with a water control. Although the Kappacin mouthrinse showed a reduction in supragingival plaque of posterior teeth of 7% when compared with the water, this reduction in plaque was not statistically different to the control. In the current study the Silness and Loe plaque index was used as changes in plaque thickness, especially along the gingival margin, are more readily observed than changes in plaque distribution over the surfaces of teeth. Therefore due to short duration of the trial (5 days) and the small number of subjects, the Silness and Loe index was deemed to be the most appropriate plaque scoring system. It has also been shown that unstained plaque scores correlate much higher than stained scores with gingivitis, dry and wet plaque weight (Loesche and Green, 1972).

Salts of zinc and tin have long been recognised as having antibacterial activity and a relatively high safety profile (Moran et al., 2000). Zinc is believed to exert its antibacterial effect by inhibiting membrane transport and metabolic processes, including glycolysis, through interactions with enzymes that contain active thiol groups (Cummins and Creeth, 1992, Opperman and Rolla, 1980; Opperman et al., 1980). The adsorption of zinc into plaque bacteria initially involves electrostatic interactions with cell surface proteins followed by their subsequent transport into the cell. The plaque inhibiting effect is thought to be a long acting bacteriostatic effect on plaque microorganisms through the retention of the ions in dental plaque and the oral cavity after rinsing (Giertsen et al., 1988). Zinc salts have been used in toothpastes and mouthrinses in combination with the antimicrobial agents triclosan, chlorhexidine and sanguinarine. These have been shown to have a synergistic antibacterial action (Giertsen et al., 1988; Moran et al., 2000).

Treatment with the Kappacin-zinc containing mouthrinse resulted in a decrease of 21% in the posterior teeth plaque index scores (FIG. 6). These results are comparable to chlorhexidine mouthrinses. Chlorhexidine is considered to be the most effective anti-plaque and anti-gingivitis compound so far tested. However side effects from the use of chlorhexidine, including extrinsic staining of teeth and restorations, taste distortion, and brown staining of tongue, limit its long term use (Elderidge et al., 1998).

It is well accepted that the accumulation of supragingival plaque over a period of time is associated with the development of gingivitis, and initiation of periodontitis and that supragingival plaque control alone is sufficient to resolve gingivitis (Corbet and Davies, 1993). The results of this study indicate that the combination of the natural peptide Kappacin with zinc ions may produce a mouthrinse with efficacy in supragingival plaque control.

Proposed Formulations Including the Composition of the Present Invention

Formulation 1

| Ingredient | % w/w |
|---|---|
| Dicalcium phosphate dihydrate | 50.0 |
| Glycerol | 20.0 |
| Sodium carboxymethyl cellulose | 1.0 |
| Sodium lauryl sulphate | 1.5 |
| Sodium lauroyl sarconisate | 0.5 |
| Flavour | 1.0 |
| Sodium saccharin | 0.1 |
| Chlorhexidine gluconate | 0.01 |
| Dextranase | 0.01 |
| Composition of present invention | 1.0 |
| Water | balance |

Formulation 2

| Ingredient | % w/w |
|---|---|
| Dicalcium phosphate dihydrate | 50.0 |
| Sorbitol | 10.0 |
| Glycerol | 10.0 |
| Sodium carboxymethyl cellulose | 1.0 |
| Sodium lauryl sulphate | 1.5 |
| Sodium lauroyl sarconisate | 0.5 |
| Flavour | 1.0 |
| Sodium saccharin | 0.1 |
| Sodium monofluorophosphate | 0.3 |
| Chlorhexidine gluconate | 0.01 |
| Dextranase | 0.01 |
| Composition of present invention | 2.0 |
| Water | balance |

Formulation 3

| Ingredient | % w/w |
|---|---|
| Dicalcium phosphate dihydrate | 50.0 |
| Sorbitol | 10.0 |
| Glycerol | 10.0 |
| Sodium carboxymethyl cellulose | 1.0 |
| Lauroyl diethanolamide | 1.0 |
| Sucrose monolaurate | 2.0 |
| Flavour | 1.0 |
| Sodium saccharin | 0.1 |
| Sodium monofluorophosphate | 0.3 |
| Chlorhexidine gluconate | 0.01 |
| Dextranase | 0.01 |
| Composition of present invention | 5.0 |
| Water | balance |

Formulation 4

| Ingredient | % w/w |
|---|---|
| Sorbitol | 10.0 |
| Irish moss | 1.0 |
| Sodium Hydroxide (50%) | 1.0 |
| Gantrez | 19.0 |
| Water (deionised) | 2.69 |
| Sodium monofluorophosphate | 0.76 |
| Sodium saccharin | 0.3 |
| Pyrophosphate | 2.0 |
| Hydrated alumina | 48.0 |
| Flavour oil | 0.95 |
| Composition of present invention | 1.0 |
| Water | balance |

Formulation 5

| Ingredient | % w/w |
|---|---|
| Sodium polyacrylate | 50.0 |
| Sorbitol | 10.0 |
| Glycerol | 20.0 |
| Sodium saccharin | 0.1 |
| Sodium monofluorophosphate | 0.3 |
| Chlorhexidine gluconate | 0.01 |
| Ethanol | 3.0 |
| Composition of present invention | 2.0 |
| Linolic acid | 0.05 |
| Water | balance |

Proposed Mouthwash Formulations

Formulation 1

| Ingredient | % w/w |
|---|---|
| Ethanol | 20.0 |
| Flavour | 1.0 |
| Sodium saccharin | 0.1 |
| Sodium monofluorophosphate | 0.3 |
| Chlorhexidine gluconate | 0.01 |
| Lauroyl diethanolamide | 0.3 |
| Composition of present invention | 2.0 |
| Water | balance |

Formulation 2

| Ingredient | % w/w |
|---|---|
| Gantrez S-97 | 2.5 |
| Glycerine | 10.0 |
| Flavour oil | 0.4 |
| Sodium monofluorophosphate | 0.05 |
| Chlorhexidine gluconate | 0.01 |
| Lauroyl diethanolamide | 0.2 |
| Composition of present invention | 2.0 |
| Water | balance |

Proposed Lozenge Formulation

| Ingredient | % w/w |
|---|---|
| Sugar | 75-80 |
| Corn syrup | 1-20 |
| Flavour oil | 1-2 |
| NaF | 0.01-0.05 |
| Composition of present invention | 3.0 |
| Mg stearate | 1-5 |
| Water | balance |

Proposed Gingival Massage Cream Formulation

| Ingredient | % w/w |
|---|---|
| White petrolatum | 8.0 |
| Propylene glycol | 4.0 |
| Stearyl alcohol | 8.0 |
| Polyethylene Glycol 4000 | 25.0 |
| Polyethylene Glycol 400 | 37.0 |
| Sucrose monostearate | 0.5 |
| Chlorohexidine gluconate | 0.1 |
| Composition of present invention | 3.0 |
| Water | balance |

Proposed Chewing Gum Formulation

| Ingredient | % w/w |
|---|---|
| Gum base | 30.0 |
| Calcium carbonate | 2.0 |
| Crystalline sorbitol | 53.0 |
| Glycerine | 0.5 |
| Flavour oil | 0.1 |
| Composition of present invention | 2.0 |
| Water | balance |

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

Addy M., Richards J. and Williams G. (1980), Effects of a Zinc Citrate Mouthwash on Dental Plaque and Salivary Bacteria, *Journal of Clinical Periodontology* 7, 309-315.

Corbet E. F. and Davies W. I. R. (1993), The Role of Supragingival Plaque in the Control of Progressive Periodontal-Disease—a Review, *Journal of Clinical Periodontology* 20, 307-313.

Creamer L. and Harris D. (1997). Relationship between milk protein polymorphism and physico-chemical properties. In: Milk Protein Polymorphism: International Dairy Federation Special Issue 9702, pp. 110-123.

Cummins D. and Creeth J. E. (1992), Delivery of Antiplaque Agents from Dentifrices, Gels, and Mouthwashes, *Journal of Dental Research* 71, 1439-1449.

Eldridge K. R., Finnie S. F., Stephens J. A., Mauad A. M., Munoz C. A. and Kettering J. D. (1998), Efficacy of an alcohol-free chlorhexidine mouthrinse as an antimicrobial agent, *Journal of Prosthetic Dentistry* 80, 685-690.

Folch J., Lees M. and Stanley G. H. S. (1957), A Simple Method for the Isolation and Purification of Total Lipides from Animal Tissues, *Journal of Biological Chemistry* 226, 497-509.

Giertesen E., Scheie A. and Gunnar R. (1998), Inhibition of plaque formation and plaque acidogenicity by zinc and chlorhexidine combinations, *Scandinavian Journal of Dental Research* 96, 541-550.

Goumon Y., Strub J. M., Moniatte M., Nullans G., Poteur L., Hubert P., VanDorsselaer A., Aunis D. and MetzBoutigue M. H. (1996), The C-terminal bisphosphorylated proenkephalin-A-(209-237)-peptide from adrenal medullary chromaffin granules possesses antibacterial activity, *European Journal of Biochemistry* 235, 516-525.

Hogg S. (1990), Chenical control of plaque, *Dental Update* 17, 332-334.

Hope, C. K., and M. Wilson. 2003. Measuring the thickness of an outer layer of viable bacteria in an oral biofilm by viability mapping. J. Microbiol. Methods 54:403-410.

Malkoski M., Dashper S. G., O'Brien-Simpson N. M., Talbo G. H., Macris M., Cross K. J. and Reynolds E. C. (2001), Kappacin, a novel antibacterial peptide from bovine milk, *Antimicrobial Agents and Chemotherapy* 45, 2309-2315.

Nikaido H., Nikaido K. and Harayama S. (1991), Identification and Characterization of Porins in *Pseudomonas-Aeruginosa*, *Journal of Biological Chemistry* 266, 770-779.

Plowman J. E., Creamer L. K., Liddell M. J. and Cross J. J. (1997), Solution conformation of a peptide corresponding to bovine kappa-casein B residues 130-153 by circular dichroism spectroscopy and H-1-nuclear magnetic resonance spectroscopy, *Journal of Dairy Research* 64, 377-397.

Shu, M., C. M. Browngardt, Y. Y. Chen, and R. A. Burne. 2003. Role of urease enzymes in stability of a 10-species oral biofilm consortium cultivated in a constant-depth film fermenter. Infect. Immun. 71:7188-7192.

Smallcombe S. H., Patt S. L. and Keifer P. A. (1995), WET solvent suppression and its applications to LC NMR and high-resolution NMR spectroscopy, *Journal of Magnetic Resonance Series A* 117, 295-303.

Smith M. H., Edwards P. J. B., Palmano K. P. and Creamer L. K. (2002), Structural features of bovine caseinomacropeptide A and B by H-1 nuclear magnetic resonance spectroscopy, *Journal of Dairy Research* 69, 85-94.

Strub J. M., Goumon Y., Lugardon K., Capon C., Lopez M., Moniatte M., VanDorsselaer A., Aunis D. and MetzBoutigue M. H. (1996), Antibacterial activity of glycosylated and phosphorylated chromogranin A-derived peptide 173-194 from bovine adrenal medullary chromaffin granules, *Journal of Biological Chemistry* 271, 28533-28540.

Talbo G. H., Suckau D., Malkoski M. and Reynolds E. C. (2001), MALDI-PSD-MS analysis of the phosphorylation sites of caseinomacropeptide, *Peptides* 22, 1093-1098.

Wilson, M. 1996. Susceptibility of oral bacterial biofilms to antimicrobial agents. J. Med. Microbiol. 44:79-87.

Wimpenny, J., A. Peters, and M. Scourfield. 1989. Modeling spatial gradients, p. 111-127. In W. Characklis and P. Wlderer (ed.), Structure and function of biofilms. John Wiley and Sons, Chichester.

The invention claimed is:

1. An antimicrobial composition, the composition comprising an aqueous solvent and having a divalent cation and a peptide dissolved therein, wherein the divalent cation is added to the solvent such that substantially all of the divalent cation is dissolved in the solvent, wherein the divalent cation is a $Ca^{2+}$ or a $Zn^{2+}$ ion, and wherein the peptide is non-glycosylated, has a length of less than about 100 amino acids, and comprises an amino acid sequence selected from the group consisting of:

Ala Val Glu Ser Thr Val Ala Thr Leu Glu Ala X Pro Glu Val Ile Glu Ser Pro Pro Glu (SEQ ID NO:1); and Ala Val Glu Ser Thr Val Ala Thr Leu Glu Asp X Pro Glu Val Ile Glu Ser Pro Pro Glu (SEQ ID NO:2), wherein amino acid residue X is a phosphoseryl residue.

2. The antimicrobial composition according to claim 1 wherein the peptide has a length of less than about 70 amino acids.

3. The antimicrobial composition according to claim 1 wherein the peptide comprises the amino acid sequence Ala Val Glu Ser Thr Val Ala Thr Leu Glu Ala X Pro Glu Val Ile Glu Ser Pro Pro Glu (SEQ ID NO:1), wherein amino acid residue X is a phosphoseryl residue.

4. The antimicrobial composition according to claim 1 wherein the peptide comprises an amino acid sequence selected from the group consisting of:

Met Ala Ile Pro Pro Lys Lys Asn Gln Asp Lys Thr Glu Ile Pro Thr Ile Asn Thr Ile Ala Ser Gly Glu Pro Thr Ser Thr Pro Thr Ile Glu Ala Val Glu Ser Thr Val Ala Thr Leu Glu Ala X Pro Glu Val Ile Glu Ser Pro Pro Glu Ile Asn Thr Val Gln Val Thr Ser Thr Ala Val (SEQ ID NO:3);

Met Ala Ile Pro Pro Lys Lys Asn Gln Asp Lys Thr Glu Ile Pro Thr Ile Asn Thr Ile Ala X Gly Glu Pro Thr Ser Thr Pro Thr Ile Glu Ala Val Glu Ser Thr Val Ala Thr Leu Glu Ala X Pro Glu Val Ile Glu Ser Pro Pro Glu Ile Asn Thr Val Gln Val Thr Ser Thr Ala Val (SEQ ID NO:4);

Met Ala Ile Pro Pro Lys Lys Asn Gln Asp Lys Thr Glu Ile Pro Thr Ile Asn Thr Ile Ala Ser Gly Glu Pro Thr Ser Thr Pro Thr Thr Glu Ala Val Glu Ser Thr Val Ala Thr Leu Glu Asp X Pro Glu Val Ile Glu Ser Pro Pro Glu Ile Asn Thr Val Gln Val Thr Ser Thr Ala Val (SEQ ID NO. 5);

Met Ala Ile Pro Pro Lys Lys Asn Gln Asp Lys Thr Glu Ile Pro Thr Ile Asn Thr Ile Ala X Gly Glu Pro Thr Ser Thr Pro Thr Thr Glu Ala Val Glu Ser Thr Val Ala Thr Leu Glu Asp X Pro Glu Val Ile Glu Ser Pro Pro Glu Ile Asn Thr Val Gln Val Thr Ser Thr Ala Val (SEQ ID NO. 6);

Thr Glu Ile Pro Thr Ile Asn Thr Ile Ala Ser Gly Glu Pro Thr Ser Thr Pro Thr Ile Glu Ala Val Glu Ser Thr Val Ala Thr Leu Glu Ala X Pro Glu Val Ile Glu Ser Pro Pro Glu Ile Asn Thr Val Gln Val Thr Ser Thr Ala Val (SEQ ID NO. 7);

Thr Glu Ile Pro Thr Ile Asn Thr Ile Ala X Gly Glu Pro Thr Ser Thr Pro Thr Ile Glu Ala Val Glu Ser Thr Val Ala Thr Leu Glu Ala X Pro Glu Val Ile Glu Ser Pro Pro Glu Ile Asn Thr Val Gln Val Thr Ser Thr Ala Val (SEQ ID NO. 8);

Thr Glu Ile Pro Thr Ile Asn Thr Ile Ala Ser Gly Glu Pro Thr Ser Thr Pro Thr Thr Glu Ala Val Glu Ser Thr Val Ala Thr Leu Glu Asp X Pro Glu Val Ile Glu Ser Pro Pro Glu Ile Asn Thr Val Gln Val Thr Ser Thr Ala Val (SEQ ID NO. 9); and Thr Glu Ile Pro Thr Ile Asn Thr Ile Ala X Gly Glu Pro Thr Ser Thr Pro Thr Thr Glu Ala Val Glu Ser Thr Val Ala Thr Leu Glu Asp X Pro Glu Val Ile Glu Ser Pro Pro Glu Ile Asn Thr Val Gln Val Thr Ser Thr Ala Val (SEQ ID NO. 10), wherein amino acid residue X is a phosphoseryl residue.

5. The antimicrobial composition according to claim 4, wherein the divalent cation is a $Ca^{2+}$ ion.

6. The antimicrobial composition according to claim 4, wherein the divalent cation is $Zn^{2+}$.

7. The antimicrobial composition according to claim 1 wherein the composition has a molar ratio of the divalent cation to the peptide in the range of 0.5-15.0:1.0.

8. The antimicrobial composition according to claim 7 wherein the molar ratio of the divalent cation to the peptide is in the range of 0.5:1.0 to 4.0:1.0.

9. The antimicrobial composition according to claim 8 wherein the molar ratio of the divalent cation to the peptide is in the range of 1.0:1.0 to 4.0:1.0.

10. The antimicrobial composition according to claim 9 wherein the molar ratio of the divalent cation to the peptide is in the range of 1.0:1.0 to 2.0:1.0.

11. A pharmaceutical composition comprising a composition according to claim 1 and a pharmaceutically acceptable carrier.

12. A method of treatment, comprising:
a) administering to a subject a therapeutically effective amount of a formulation comprising:
an aqueous solvent and having a divalent cation and a peptide dissolved therein, wherein the divalent cation is added to the solvent such that substantially all of the divalent cation is dissolved in the solvent, wherein the divalent cation is a $Ca^{2+}$ or a $Zn^{2+}$ ion,
and wherein the peptide is non-glycosylated, has a length of less than about 100 amino acids, and comprises an amino acid sequence selected from the group consisting of:

Ala Val Glu Ser Thr Val Ala Thr Leu Glu Ala X Pro Glu Val Ile Glu Ser Pro Pro Glu (SEQ ID NO:1); and Ala Val Glu Ser Thr Val Ala Thr Leu Glu Asp X Pro Glu Val Ile Glu Ser Pro Pro Glu (SEQ ID NO:2), wherein amino acid residue X is a phosphoseryl residue ;and b) allowing the formulation to act on the subject in a manner which prevents a disease selected from the group consisting of dental caries and periodontal disease.

13. The method of claim 12, wherein the administering is directly to the teeth or gums of the subject.

14. A method of claim 12, wherein the administering is by topical administration.

15. An antimicrobial composition according to claim 1 wherein the divalent cation is $Zn^{2+}$.

16. An antimicrobial composition according to claim 1 wherein the divalent cation is $Ca^{2+}$.

17. The antimicrobial composition according to claim 1 wherein the peptide comprises the amino acid sequence Ala Val Glu Ser Thr Val Ala Thr Leu Glu Asp X Pro Glu Val Ile Glu Ser Pro Pro Glu (SEQ ID NO:2), wherein amino acid residue X is a phosphoseryl residue.

* * * * *

UNITED STATES PATENT AND TRADEMARK OFFICE
CERTIFICATE OF CORRECTION

| | | |
|---|---|---|
| PATENT NO. | : 8,106,152 B2 | Page 1 of 1 |
| APPLICATION NO. | : 10/596623 | |
| DATED | : January 31, 2012 | |
| INVENTOR(S) | : Eric Charles Reynolds et al. | |

It is certified that error appears in the above-identified patent and that said Letters Patent is hereby corrected as shown below:

On the Title Page in the "Inventors" Section Item (75) should read

Eric Charles Reynolds, Balwyn, VIC (AU);
Stuart Geoffrey Dashper, Brunswick East, VIC (AU);
Rita Ann Paolini, Kew (AU)

Signed and Sealed this
Twelfth Day of February, 2013

Teresa Stanek Rea
*Acting Director of the United States Patent and Trademark Office*

SEQUENCE LISTING

<160> NUMBER OF SEQ ID NOS: 10

<210> SEQ ID NO 1
<211> LENGTH: 21
<212> TYPE: PRT
<213> ORGANISM: Artificial Sequence
<220> FEATURE:
<223> OTHER INFORMATION: Antimicrobial Peptide
<221> NAME/KEY: PHOSPHORYLATION
<222> LOCATION: (12)...(12)

<400> SEQUENCE: 1

Ala Val Glu Ser Thr Val Ala Thr Leu Glu Ala Ser Pro Glu Val Ile
 1               5                  10                  15

Glu Ser Pro Pro Glu
            20

<210> SEQ ID NO 2
<211> LENGTH: 21
<212> TYPE: PRT
<213> ORGANISM: Artificial Sequence
<220> FEATURE:
<223> OTHER INFORMATION: Antimicrobial Peptide
<221> NAME/KEY: PHOSPHORYLATION
<222> LOCATION: (12)...(12)

<400> SEQUENCE: 2

Ala Val Glu Ser Thr Val Ala Thr Leu Glu Asp Ser Pro Glu Val Ile
 1               5                  10                  15

Glu Ser Pro Pro Glu
            20

<210> SEQ ID NO 3
<211> LENGTH: 64
<212> TYPE: PRT
<213> ORGANISM: Artificial Sequence
<220> FEATURE:
<223> OTHER INFORMATION: Antimicrobial Peptide
<221> NAME/KEY: PHOSPHORYLATION
<222> LOCATION: (44)...(44)

<400> SEQUENCE: 3

Met Ala Ile Pro Pro Lys Lys Asn Gln Asp Lys Thr Glu Ile Pro Thr
 1               5                  10                  15

Ile Asn Thr Ile Ala Ser Gly Glu Pro Thr Ser Thr Pro Thr Ile Glu
            20                  25                  30

Ala Val Glu Ser Thr Val Ala Thr Leu Glu Ala Ser Pro Glu Val Ile
        35                  40                  45

Glu Ser Pro Pro Glu Ile Asn Thr Val Gln Val Thr Ser Thr Ala Val
    50                  55                  60

<210> SEQ ID NO 4
<211> LENGTH: 64
<212> TYPE: PRT
<213> ORGANISM: Artificial Sequence
<220> FEATURE:
<223> OTHER INFORMATION: Antimicrobial Peptide
<221> NAME/KEY: PHOSPHORYLATION
<222> LOCATION: (22)...(22)
<221> NAME/KEY: PHOSPHORYLATION
<222> LOCATION: (44)...(44)

<400> SEQUENCE: 4

Met Ala Ile Pro Pro Lys Lys Asn Gln Asp Lys Thr Glu Ile Pro Thr
 1               5                  10                  15

```
Ile Asn Thr Ile Ala Ser Gly Glu Pro Thr Ser Thr Pro Thr Ile Glu
         20                  25                  30

Ala Val Glu Ser Thr Val Ala Thr Leu Glu Ala Ser Pro Glu Val Ile
         35                  40                  45

Glu Ser Pro Pro Glu Ile Asn Thr Val Gln Val Thr Ser Thr Ala Val
 50                  55                  60

<210> SEQ ID NO 5
<211> LENGTH: 64
<212> TYPE: PRT
<213> ORGANISM: Artificial Sequence
<220> FEATURE:
<223> OTHER INFORMATION: Antimicrobial Peptide
<221> NAME/KEY: PHOSPHORYLATION
<222> LOCATION: (44)...(44)

<400> SEQUENCE: 5

Met Ala Ile Pro Pro Lys Lys Asn Gln Asp Lys Thr Glu Ile Pro Thr
 1               5                  10                  15

Ile Asn Thr Ile Ala Ser Gly Glu Pro Thr Ser Thr Pro Thr Thr Glu
         20                  25                  30

Ala Val Glu Ser Thr Val Ala Thr Leu Glu Asp Ser Pro Glu Val Ile
         35                  40                  45

Glu Ser Pro Pro Glu Ile Asn Thr Val Gln Val Thr Ser Thr Ala Val
 50                  55                  60

<210> SEQ ID NO 6
<211> LENGTH: 64
<212> TYPE: PRT
<213> ORGANISM: Artificial Sequence
<220> FEATURE:
<223> OTHER INFORMATION: Antimicrobial Peptide
<221> NAME/KEY: PHOSPHORYLATION
<222> LOCATION: (22)...(22)
<221> NAME/KEY: PHOSPHORYLATION
<222> LOCATION: (44)...(44)

<400> SEQUENCE: 6

Met Ala Ile Pro Pro Lys Lys Asn Gln Asp Lys Thr Glu Ile Pro Thr
 1               5                  10                  15

Ile Asn Thr Ile Ala Ser Gly Glu Pro Thr Ser Thr Pro Thr Thr Glu
         20                  25                  30

Ala Val Glu Ser Thr Val Ala Thr Leu Glu Asp Ser Pro Glu Val Ile
         35                  40                  45

Glu Ser Pro Pro Glu Ile Asn Thr Val Gln Val Thr Ser Thr Ala Val
 50                  55                  60

<210> SEQ ID NO 7
<211> LENGTH: 53
<212> TYPE: PRT
<213> ORGANISM: Artificial Sequence
<220> FEATURE:
<223> OTHER INFORMATION: Antimicrobial Peptide
<221> NAME/KEY: PHOSPHORYLATION
<222> LOCATION: (33)...(33)

<400> SEQUENCE: 7

Thr Glu Ile Pro Thr Ile Asn Thr Ile Ala Ser Gly Glu Pro Thr Ser
 1               5                  10                  15

Thr Pro Thr Ile Glu Ala Val Glu Ser Thr Val Ala Thr Leu Glu Ala
         20                  25                  30

Ser Pro Glu Val Ile Glu Ser Pro Pro Glu Ile Asn Thr Val Gln Val
         35                  40                  45
```

Thr Ser Thr Ala Val
    50

<210> SEQ ID NO 8
<211> LENGTH: 53
<212> TYPE: PRT
<213> ORGANISM: Artificial Sequence
<220> FEATURE:
<223> OTHER INFORMATION: Antimicrobial Peptide
<221> NAME/KEY: PHOSPHORYLATION
<222> LOCATION: (11)...(11)
<221> NAME/KEY: PHOSPHORYLATION
<222> LOCATION: (33)...(33)

<400> SEQUENCE: 8

Thr Glu Ile Pro Thr Ile Asn Thr Ile Ala Ser Gly Glu Pro Thr Ser
1               5                   10                  15

Thr Pro Thr Ile Glu Ala Val Glu Ser Thr Val Ala Thr Leu Glu Ala
            20                  25                  30

Ser Pro Glu Val Ile Glu Ser Pro Pro Glu Ile Asn Thr Val Gln Val
        35                  40                  45

Thr Ser Thr Ala Val
    50

<210> SEQ ID NO 9
<211> LENGTH: 53
<212> TYPE: PRT
<213> ORGANISM: Artificial Sequence
<220> FEATURE:
<223> OTHER INFORMATION: Antimicrobial Peptide
<221> NAME/KEY: PHOSPHORYLATION
<222> LOCATION: (33)...(33)

<400> SEQUENCE: 9

Thr Glu Ile Pro Thr Ile Asn Thr Ile Ala Ser Gly Glu Pro Thr Ser
1               5                   10                  15

Thr Pro Thr Thr Glu Ala Val Glu Ser Thr Val Ala Thr Leu Glu Asp
            20                  25                  30

Ser Pro Glu Val Ile Glu Ser Pro Pro Glu Ile Asn Thr Val Gln Val
        35                  40                  45

Thr Ser Thr Ala Val
    50

<210> SEQ ID NO 10
<211> LENGTH: 53
<212> TYPE: PRT
<213> ORGANISM: Artificial Sequence
<220> FEATURE:
<223> OTHER INFORMATION: Antimicrobial Peptide
<221> NAME/KEY: PHOSPHORYLATION
<222> LOCATION: (11)...(11)
<221> NAME/KEY: PHOSPHORYLATION
<222> LOCATION: (33)...(33)

<400> SEQUENCE: 10

Thr Glu Ile Pro Thr Ile Asn Thr Ile Ala Ser Gly Glu Pro Thr Ser
1               5                   10                  15

Thr Pro Thr Thr Glu Ala Val Glu Ser Thr Val Ala Thr Leu Glu Asp
            20                  25                  30

Ser Pro Glu Val Ile Glu Ser Pro Pro Glu Ile Asn Thr Val Gln Val
        35                  40                  45

Thr Ser Thr Ala Val
    50